United States Patent
Han et al.

(10) Patent No.: US 9,845,478 B2
(45) Date of Patent: Dec. 19, 2017

(54) COMPOSITIONS AND METHODS FOR XYLEM-SPECIFIC EXPRESSION IN PLANT CELLS

(75) Inventors: Kyung-Hwan Han, Okemos, MI (US); Jae-Heung Ko, Yongin-si (KR)

(73) Assignee: Board of Trustees of Michigan State University, East Lansing, MI (US)

( * ) Notice: Subject to any disclaimer, the term of this patent is extended or adjusted under 35 U.S.C. 154(b) by 545 days.

(21) Appl. No.: 13/821,095

(22) PCT Filed: Sep. 13, 2011

(86) PCT No.: PCT/US2011/051371
§ 371 (c)(1),
(2), (4) Date: Jun. 12, 2013

(87) PCT Pub. No.: WO2012/037107
PCT Pub. Date: Mar. 22, 2012

(65) Prior Publication Data
US 2013/0254930 A1    Sep. 26, 2013

Related U.S. Application Data

(60) Provisional application No. 61/382,734, filed on Sep. 14, 2010.

(51) Int. Cl.
*C12N 15/113*  (2010.01)
*C12N 15/82*   (2006.01)
*C07K 14/415*  (2006.01)

(52) U.S. Cl.
CPC ........ *C12N 15/8223* (2013.01); *C07K 14/415* (2013.01); *C12N 15/113* (2013.01);
(Continued)

(58) Field of Classification Search
None
See application file for complete search history.

(56) References Cited

U.S. PATENT DOCUMENTS

| 5,451,514 A | 9/1995 | Boudet et al. |
| 6,066,780 A | 5/2000 | Boudet et al. |

(Continued)

FOREIGN PATENT DOCUMENTS

WO    WO-94/23044 A1    10/1994

OTHER PUBLICATIONS

Dejardin et al. Ptajxtjxt3F12F12F1212 Poplar cDNA library from young tension xylem Populus tremula x Populus alba. GenBank Accession No. CF237236. Published Aug. 5, 2003. pp. 1-2.*

(Continued)

*Primary Examiner* — Ashley K Buran
(74) *Attorney, Agent, or Firm* — Schwegman Lundberg & Woessner, P. A.

(57) ABSTRACT

The invention provides promoter sequences that regulate specific expression of operably linked sequences in developing xylem cells and/or in developing xylem tissue. The developing xylem-specific sequences are exemplified by the DX5, DX8, DX11, and DX15 promoters, portions thereof, and homologs thereof. The invention further provides expression vectors, cells, tissues and plants that contain the invention's sequences. The compositions of the invention and methods of using them are useful in, for example, improving the quantity (biomass) and/or the quality (wood density, lignin content, sugar content etc.) of expressed biomass feedstock products that may be used for bioenergy, biorefinary, and generating wood products such as pulp, paper, and solid wood.

17 Claims, 12 Drawing Sheets

(52) U.S. Cl.
CPC ......... *C12N 15/82* (2013.01); *C12N 15/8216* (2013.01); *C12N 15/8226* (2013.01); *C12N 15/8227* (2013.01); *C12N 15/8246* (2013.01); *C12N 15/8255* (2013.01)

(56) References Cited

U.S. PATENT DOCUMENTS

| | | | |
|---|---|---|---|
| 6,204,434 | B1 | 3/2001 | Bloksberg et al. |
| 6,252,135 | B1 | 6/2001 | Chiang et al. |
| 6,380,459 | B1 | 4/2002 | Perera et al. |
| 7,365,186 | B2 | 4/2008 | Phillips et al. |
| 7,402,428 | B2 | 7/2008 | Forster et al. |
| 7,442,786 | B2 | 10/2008 | Phillips et al. |
| 7,999,149 | B2 | 8/2011 | Phillips et al. |
| 8,030,545 | B2 | 10/2011 | Forster et al. |
| 8,389,806 | B2 | 3/2013 | Phillips et al. |
| 2006/0101535 | A1 | 5/2006 | Forster et al. |
| 2009/0113574 | A1* | 4/2009 | Byrum et al. ............. 800/298 |
| 2009/0178163 | A1 | 7/2009 | Wu et al. |
| 2013/0213592 | A1 | 8/2013 | Forster |

OTHER PUBLICATIONS

Hatton et al. Two classes of cis sequences contribute to tissue-specific expression of a PAL2 promoter in transgenic tobacco. The Plant Journal. 1995. 7(6): 859-876.*

Torres-Schumann et al. In vitro binding of the tomato bZIP transcriptional activator VSF-1 to a regulatory elements that control xylem-specific gene expression. The Plant Journal. 1996. 9(3): 283-296.*

Wu et al. A xylem-specifci cellulose synthase gene from aspen (*Populus tremuloides*) is responsive to mechanical stress. The Plant Journal. 2000. 22(6): 495-502.*

Ko et al. Tissue-type-specific transcriptome analysis identifies developing xylem-specific promoters in poplar. Plant Biotechnology Journal. 2012. 10:587-596.*

Moyle et al. Isolation and characterization of a Pinus radiata lignin biosynthesis-related O-methyltransferase promoter. Plant Cell Rep. 2002. 20:1052-1060.*

Lafarguette et al. Poplar genes encoding fasciclin-like arabinogalactan proteins are highly expressed in tension wood. New Phytologist. 2004. 164:107-121.*

Lafarguette et al. Populus alba x Populus tremula fasciclin-like AGP 18 (FLA8). GenBank Accession No. AY607760. published Jun. 15, 2006. pp. 1-2.*

Tuskan et al. The genome of black cottonwood, *Populus trichocarpa* (Torr. & Gray). Science. 2006. 313:1596-1604.*

Tuskan et al. Populus trichocarpa predicted protein. GenBank Accession No. XM_002313483. published Dec. 4, 2009. pp. 1-2.*

Boerjan et al. Lignin biosynthesis. Annu. Rev. Plant Biol. 2003. 54:519-546.*

Clontech. GenomeWalker Universal Kit User Manual. Clontech Laboratories. 2007. pp. 1-30.*

Populus trichocarpa linkage group IX, whole genome shotgun sequence. GenBank Accession No. NC_008475. Published Oct. 17, 2006. pp. 1-3.*

"International Application Serial No. PCT/US2011/051371, International Preliminary Report on Patentability dated Mar. 28, 2013", 6 pgs.

"International Application Serial No. PCT/US2011/051371, Written Opinion dated Jan. 20, 2012", 4 pgs.

Bonke, M., et al., "APL regulates vascular tissue identity in *Arabidopsis*", *Nature*, 426(6963), (2003), 181-186.

Curtis, M. D., et al., "A Gateway Cloning Vector Set for High-Throughput Functional Analysis of Genes in Planta", *Plant Physiology*, 133(2), (2003), 462-469.

Dharmawardhana, D. P., et al., "cDNA cloning and heterologous expression of coniferin beta-glucosidase", *Plant Mol. Biol.*, 40(2), (1999), 365-372.

Feuillet, C., et al., "Tissue- and cell-specific expression of a cinnamyl alcohol dehydrogenase promoter in transgenic poplar plants", *Plant Molecular Biology*, 27(4), (1995), 651-667.

Han, K.-H., et al., "An *Agrobacterium tumefaciens* transformation protocol effective on a variety of cottonwood hybrids (genus *Populus*)", *Plant Cell Reports*, 19(3), (2000), 315-320.

Hu, W.-J., et al., "Repression of lignin biosynthesis promotes cellulose accumulation and growth in transgenic trees", *Nature Biotechnology*, 17(8), (1999), 808-812.

Jones, L., et al., "Cloning and characterization of irregular xylem4 (irx4): a severely lignin-deficient mutant of *Arabidopsis*", *The Plant Journal*, 26(2), (2001), 205-216.

Keller, B., et al., "Vascular expression of a bean cell wall glycine-rich protein—glucuronidase gene fusion in transgenic tobacco", *The EMBOL Journal*, 8(5), (1989), 1309-1314.

Kerstetter, R. A., et al., "KANADI regulates organ polarity in *Arabidopsis*", *Nature*, 411(6838), (2001), 706-709.

Leple, J. C., et al., "Transgenic poplars: expression of chimeric genes using four different constructs", *Plant Cell Reports*, 11(3), (1992), 137-141.

Li, L., et al., "Combinatorial modification of multiple lignin traits in trees through multigene cotransformation", *Proc. Natl. Acad. Sci. USA*, 100(8), (2003), 4939-4944.

Murashige, T., et al., "A Revised Medium for Rapid Growth and Bio Assays with Tobacco Tissue Cultures", *Physiologia Plantarum*, 15(3), (1962), 473-497.

No, E.-G., et al., "Sequences upstream and downstream of two xylem-specific pine genes influence their expression", *Plant Science*, 160, (2000), 77-86.

Rajangam, A. S., et al., "MAP20, a Microtubule-Associated Protein in the Secondary Cell Walls of Hybrid Aspen, Is a Target of the Cellulose Synthesis Inhibitor 2,6-Dichlorobenzonitrile", *Plant Physiology*, 148(3), (2008), 1283-1294.

Song, J., et al., "Genetic Transformation of Populus trichocarpa Genotype Nisqually-1: A Functional Genomic Tool for Woody Plants", *Plant Cell Physiol.*, 47(11), (2006), 1582-1589.

Teymouri, F., et al., "Optimization of the ammonia fiber explosion (AFEX) treatment parameters for enzymatic hydrolysis of corn stover", *Bioresource Technology*, 96(18), (2005), 2014-2018.

Torres-Schumann, S., et al., "In vitro binding of the tomato bZIP transcriptional activator VSF-1 to a regulatory element that controls xylem-specific gene expression", *The Plant Journal*, 9(3), (1996), 283-296.

Turner, S. R., et al., "Collapsed Xylem Phenotype of Arabidopsis Identifies Mutants Deficient in Cellulose Deposition in the Secondary Cell Wall", *The Plant Cell*, 9(5), (1997), 689-701.

Xiang, C., et al., "A mini binary vector series for plant transformation", *Plant Molecular Biology*, 40(4), (1999), 711-717.

Zhao, C., et al., "Exploiting Secondary Growth in Arabidopsis. Consruction of Xylem and Bark cDNA Libraries and Cloning of Three Xylem Endopeptidases", *Plant Physiology*, 123(3), (2000), 1185-1196.

"International Application Serial No. PCT/US2011/051371, International Search Report dated Jan. 20, 2012", 3 pgs.

* cited by examiner

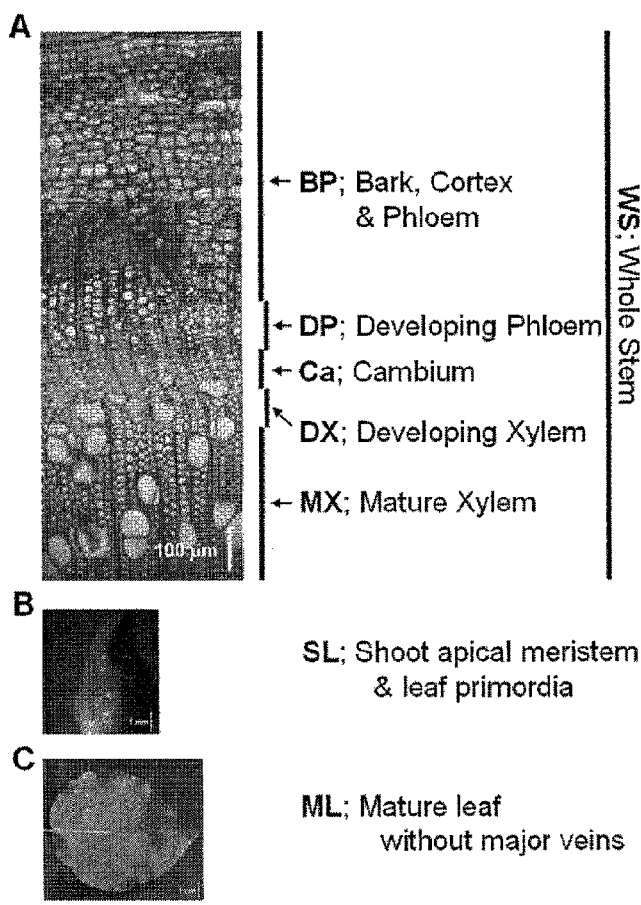

Figure 1. Sampling scheme for tissue-type specific whole transcriptome analysis.
Actively growing young poplar stems (one-year-old) were used to collect each cell-type, such as BP (bark and mature phloem cells), DP (developing phloem cells), Ca (cambium cells), DX (developing xylem cells) and MX (mature xylem cells) (A). Whole stem (WS) was used as a positive as well as an internal control. In addition, SL (SAM and leaf primordia) (B) and ML (mature leaf without major veins) (C) were included as negative controls for wood formation and internal control for meristem development.

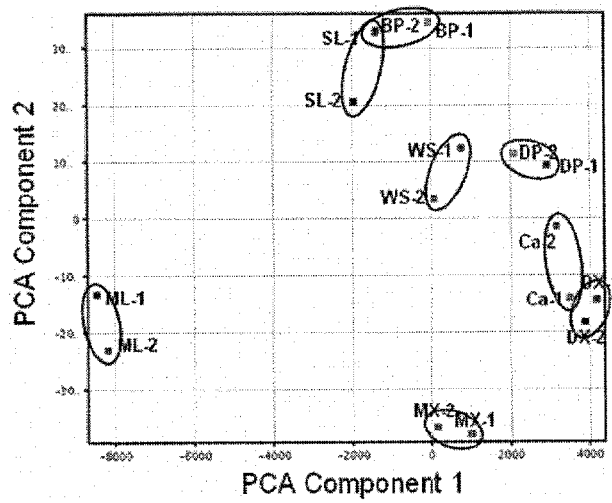

Figure 2. Principal component analysis. We used principal component analysis (PCA) as an unbiased method of comparing the results of sample. A score plot of the first two principal components (above) will cluster samples with similar expression patterns for all the genes closely together. The result shows that the individual biological replicates (e.g., July and August sample) clustered closely together and were clearly separated from those of the next sample (these cell-types are flanking each other), demonstrating that the results were reproducible and the resolution was sufficient to distinguish the individual samples from each other.

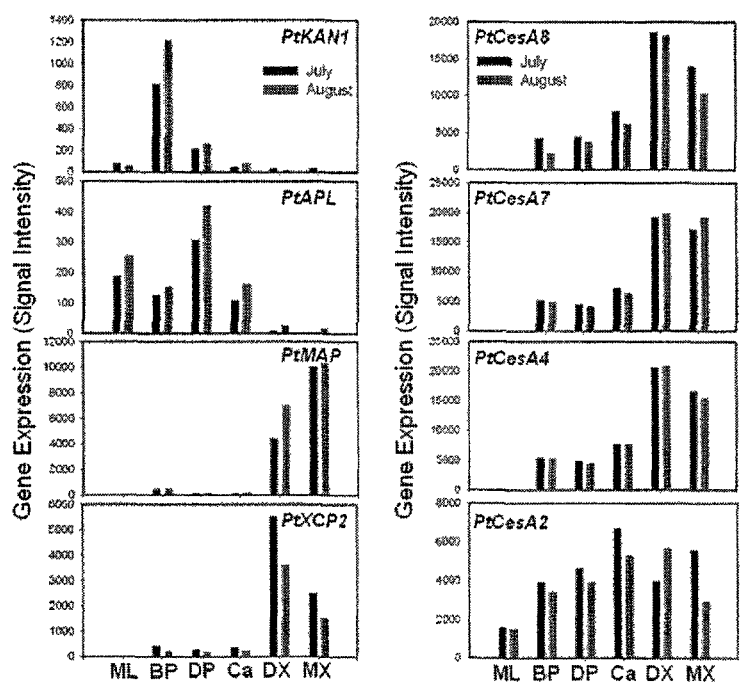
Figure 3. Validation of GeneChip data by using cell-type specific marker genes. Signal intensity obtained from genechip analysis was used as gene expression.

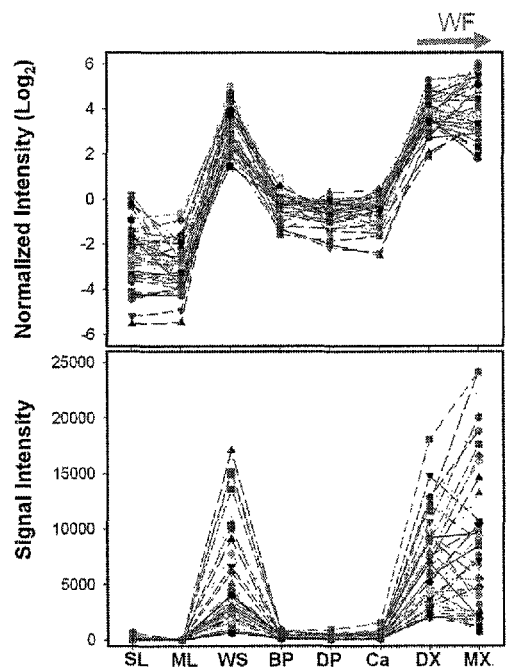
Figure 4. Identification of developing xylem (DX) specific genes.

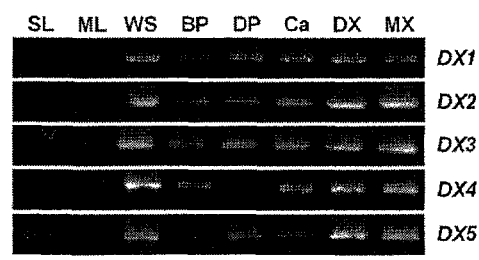
Figure 5. Confirmation of DX specific expression of selected genes by using semi-quantitative RT-PCR.

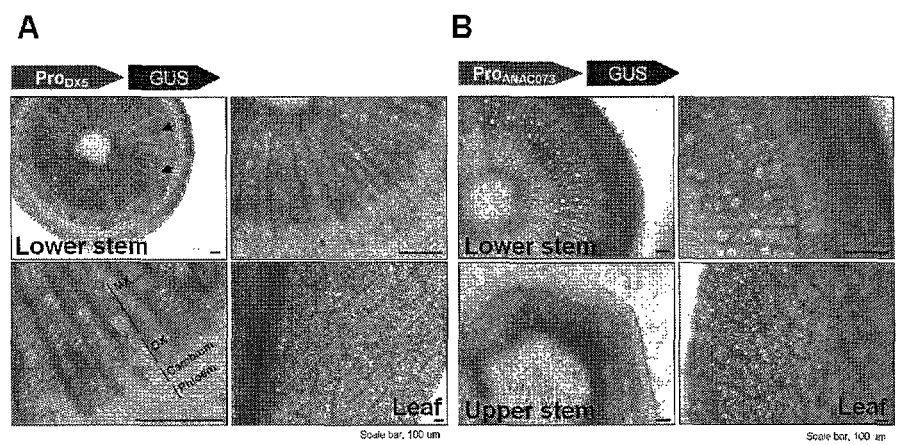

Figure 6. Developing xylem specific *GUS* gene expression driven by promoters of both *PtrNAC073* (DX5) and *ANAC073* in poplar.
A, Stem cross-section of transgenic poplar having *PtrNAC073* (DX5) promoter::GUS construct. B, Stem cross-section of transgenic poplar having *ANAC073* promoter::GUS construct. *GUS* gene expression is shown in blue color by GUS staining. Note that leaves have no *GUS* expression. Scale bar indicate 100 μm.

Figure 7

Upstream genomic sequences (1941 bp) of the Poplar gene model estExt_fgenesh4_pg.C_640203, comprising the DX5 promoter sequence

```
GGGGCAGATGATACCTTGATACTTGGACTAGGAATATTCAAAGGAGAAAATATTGAT
GTGTATATTTGTACTTAATTATGCACATCTCTTTCACTTTGTTGTAAGCTGGCAATA
TACAACACAAGAATGGTCTTTATGCTTTGATTTTCTTTTCTCACAAGAAGGTAGATA
TTGGCTTTTTACCGAAATGAATATTGCTTGAGCTAGAGAATACATCAAGTATCGTAA
AGGGCACCCCAAATTCTTACAGCCTCGTGATGCACGTTTTGTTCTTCAAAATCTAGG
GGAAATTCATTAATTGAAGGTCGGATCTGTAGGTAGAATTTCCCTTTTCTTTTTAAT
GGAATTTGATGAAAGACACTGTAGCAATAATTTAAAAGGAAATTAAGTAAGTTCACG
GTTTTTGATGGTTTTTCCCGAGTTGATTGGATCGCAGATTAACCTGAGTTTTTAAAC
GGATTACATCAATTAAATTTTTGTTTATTTTTATTGAAATTTAGTCTAATCTAAATC
CCGGGTTATTCAATCCGTCGAATAATCAAGTAAGTTTATAAAAAAAATATAATAAAA
GACAATAAAGGCTAACTATTTGTGTGGGAAGCAGACAATTCCGATGGTGTAAGAAAT
TTGTGTTGTCATTTTTTATTTATTAAATTGCTCTCCTTTTTTACAGGAATGTTATAA
ATACAAGGACATATAATTCAGCTCAATAAATCTTTTGGCTTTAATTTATTTTTCTTG
GAACAAGGGGCTGTTACCAAATATGGAGCACTGTGCTTGTGTCATGCATGTAGGTAA
GGGGGGAAAAAACTAAGGAATTTAGCTGAGAAAGAGGTTGTCAATTTACTGTGATAG
ATAGGTTCCTTGCTTTACATGAGAAGTCTACGTGAAGAAATGGAATTATATATTTGG
TTGGACATTGGCTCTCTTAATATTTATTAATTATTATTCCATTTTATCCTGTGATAT
TAAACCTAACTCCTCTTGAATAATCGGGTTGAATTGATATTTAATTAACTTGATATA
TCAAGTATCAAAACTTAATTTGATATTTTAAAAATAATATTGTTTTGATTTTTTTT
AAATATTGATTTAGATTATTTTTTATAATTTGAATCATAGTTAGATAAATTTTGAGT
TAGGTTTTATAATTATTATTTTATTAGTTTCTTTCTTATTTATGTTTTTCAATATTA
AGGAGTTTATACATTAGCTTTGTTCACACTCTAGGTTGACATTGGAGCTGAAATATC
TCTCTCTATGAGGTGGTGAAATAGCTCTCACGCATCAGATTGCCCCATCTCCACTCA
ACCCTAACTAGCCATGATTAATATTTTATTTCTTTTTTTTTTAATTTTTTTAATCTT
TAAAACTTATTTCAAGCAGAAAAACATGCCTTTAGACGGAGTAAAAAGGACCCTAAA
ACTACATTTATTGTCCTACAAGTTTTCATAAGCATCCCATTTACATAAGCACACCAC
CAAACTTAAGATCCAAGCAACCCTAAAATTTTCCTTTCTTTGCAACATACTACTACT
ACTGCATTTTTGGAAATTACACCATATTTTGATTTTTTAGGTATACCTTTCTCTCTC
TCTCTCTCTCTCCCACTCTCTCGAGAAAGGACAAAGAGGTGGTAGGGGGGAGGGG
AGAGGAGAGGAGAGGAGAGTGTGCATGTTGTCTCATGCAAAAGTGGAGGAGAATTTA
ATTCCTTCCCTACCCTAAAGATCAAGAGCTATCTATGTCTTGAAGAAAGACAATACA
TGCTTTAGAAGGAGACAAATTGCTTTTCCTTCTTTTCTTTTAAGCCCTTCGTGTCTC
TCTTCCACACACACACGCATCATACATAGTCTTTGTCTATTTTGGAGTAGCAGTT
GTCGAGGGAGAGAGCAAGAAAGAAAGGTGTGCAATATATGGGCATAAGAGGAAACCA
AAG
```

Figure 8

Upstream genomic sequences (1517 bp) of the Poplar gene model eugene3.02290017, comprising the DX8 promoter sequence.

TCCATTCTACTGGACTTCCCACCTCACCCAACTCCGAAAGAGTCCTCTCAACTAGAA
AGGAAAAAAAAAAGAAAGAGGTAAATTAAAAAAAATCACAACAACGTAAACAGACTT
TCATTTTTGTACCTGAAGAGTTTGAGGGAGGAACTTGGTTCCAACATTGAGGAACAA
CATGGCTAAGAGATCAGATTTTGCACAGAAGCTGTTGGAAGATCTCCGGTCGAGGAA
GGAACGAATGGCTGTATCTCATAGCTCAGAAGGTTCAAAATCAGCTGCTCCAGGTTA
GTATTCTATTATATTTCACAATTTATTTTCTTCAGCTCCAAAACAAAATTGAAAATT
TAGAAGGCTTAAAGCAAGTAAAAGCTATGGTTTAAGACTATCACGCAACTTGAAAAG
CTATCATGCCTCTAAACATGAAGAATCGCAAGTTTTTATCATCAGTTCAGTTCTCAT
CAGAAGTGTAAAATTAATAGCTAGGTCTCTAAACTAAATTAATGATTATTCTTACTC
AATGACCTTACCTGCTCTTTTAAGTAAAGTATAAGAAGATTATTTGGATGGCCGATT
TGGAATACAAAAGAGCAGGGATTAATAGAAAGTATGAAATGGCTAAGTTAAGAAAAT
AAAAATAAATTCAGACACCTCGCTGATGACAGAAGCAGGGCCTGCCTTCCACCTTCA
TTCAAAAACGATAGAACAAGGAGCAAGTAACCTAGTCTCGTAGTAGTATAATAATGC
TACTTGTGATGCAGTTTCCCAACCAAAAACTCTTGTGATATGCTAATAATGCTCTGT
TCCAGAAAAATCTAAAAATGAACAGAAACTTGATGAAAACAGTGGCGAAGGGTAAGA
TGAAAGAAAACCAAATATTAAAGCTTTACACCCTCTCATATGTAAAGAGCACAAAAT
GAAAAGGAAAAGAAAATCAATTCATCCATTGCAAAATATTTATATGAGAATTCCAAT
TTTCCAGTATTTTCTATTTTCAAAAAGAATAAATAGGAAAAGAAAAAAAAGACATTT
TCTATAGTGTGAACTGTGTGAGAAGAAGCAATATTAGCGCTTTATTTTCAATACTAA
GAGAAATAAAATGTCAGGAAATGATCTAAAACTAGATAGTGACATCTAGTCTTCTAG
CATACAAAAATTCCTGCATTTCCATTACTTAGTACGAAGTATCATCATTGTTTTCTC
TGCATCGTGTGCTTGTGCAGATGTACATGCTTATTCCAAGCAAATACACAGAGGATC
CAGAGATATGAAGACCCATAGAAGTGTAAGTATCATGGCTCAAGCTTATCACAGTTT
TAGGTATTATAAATTCCCAATTTACTCGAACTGTTCCATGACCACAGAATGGCATTA
GAAGTGGAAGTGTGCACAGTAGAACTAGTGGAAGTAATATAGCACTCTCCATTGAAG
AAGTTTCAACAGAGATTGTTCCATTTGGGGGAGGTCGAAACTCCGAACAAATAGGAG
ATCTGTCCATGGCACTGGCTTTTGCCCTTGAGAAT

Figure 9

Upstream genomic sequences (1315 bp) of the Poplar gene model estExt_Genewise1_v1.C_LG_III1078, comprising the DX11 promoter sequence AGTCGGTATTTCAGTACTTGGGGCCATGAAGTCAGTAGTGAAGTCTAATAAATATTC
TTAAGTTGCAAGTCTCTCTTCTGTCGCCCACGTTCTCTTCTTTGCCCTTTCTTTTTC
TTTCACATCCACAGCCTCTTTGAAACTATACTGTAATGAATAATAATCAAAACCAAG
TTCCTGTTCCTTGTTTGTGGTTTTTTCTCTCCAAATTTTGTTATCTTATCTTTCTAT
GATCCCTCTCTTCTCTCACTCCCACCTCACAAGTTTTTTAAAAAAACAAATTGTTCA
TCGGGCTTGTGACTAGAAGAAGACTGCTTACCATGTTTTTCTTTTTCGAATACAACT
TCAAAAGAAAAAAAAATGTGTCAAAAAAGGTGAACTAGGTGGAGTGTTGTGTTGACA
ATGATTCAGTACCCGTCATGGACGGGATGATTAAGATGTCAAGTGCTATTACAACTC
AAAAGCATTATTGCATCATCTGTACCGTAATGAAATTCAATGATAATCCATTAGCAC
CCAGAGCCGTCGAGAAAGGAAATGTTTAGAAGTACAATAGTGAGTAATTTTCAATCA
AAATTATAAATATATTAAAATATTATTTTTTTTATTTTTTAAAAATTAATTTTAATA
TCATAATCTGATCATACTAAAAAAATATTTTTAAAACATAAAAAGCGAAAAAAATAT
CAACAACGAATTGTAAATGGCCACCTAATCATAATATGCGGGAATTAAATTCTGTGT
GGCCAAATTTACCAGAAGATAGAAGCTGAAAATGAGCTGACAGGTTAGCAGATGATC
TTGATCGTGGTTTTCTCTGGAAGACTTGCTTGTTCGAGAACTTAACAAAGGACACAA
GCTGTTGTTGTTTTCATTTGGCACAGGTTGCTTATGAATCAAGTTCACCAACAAAAC
AAAAACAGAGAGATAAAAGGGAAAGGTTCGGTTAACTGCTGCTAAATAGAAGTCATG
TGTGTCCCTGAACAAGAAACTCCAACTTTATGTCTTAATTATGAGAAATTTTTACCA
CCTTAAATTTAAATAAGAGTGCAGGAGAGATATAACCCAAAGCTTCAGCGTCACCTA
CTTCTGCAGTCTTACCTTTTAAGCAAATACACGCACCAAAGTTCCCAGCCATCATTC
TCTATCTTTTCCATTCCCTCTCAATACTTGGTTGATTTTCAAGCAACTCAAAACAGA
ATGCTACCAGAGTTTAGCAGTCCAGGAACCTCTCACAGCACTTCCACGTTTTAGCAA
TCCAAATATTCCTGAGTTGCGGCAAGGCAATATCTTAGAGGCCGTCAGATGGGTTCG
TTCC

Figure 11

Upstream genomic sequences (1025 bp) comprising the DX15 promoter sequence.

TTCCCCCTTTTGGTTCAATGCCTTTTATTCTTCCAAAATTATTTCATATTTTGTATC
CGGAGGACATATTTGTTTCAAAAGGTGTCAGAAAATCAAAGCCCATTGAAAATATAT
AAACATATATAGATATAAAAACTCAAGGGTTCATTCCAAAATATAAGAACAAACTGA
TTGAATTAATTTGTTATTTTAAGAACACTGTCTATATGTTTATATAGTGGGAGGTAG
TGTTTTTTAAATCATATACTAACTTATTATAAAAATAAATCATAAAAAAGGAACCTC
AAGCATCCCCTGGTAAGCTCGTATGTAGGAATACTCGGAGATCAAATGTCCGAATGT
CAAATGTTAAGGCAAGTGAAATATCCCTGACTTTTTAGCAAGCAAATTGTTGAGTAG
CTAAAATGAATTATTTTAATATTTTTAAATCATTTTAATATATTAATATTAAAAAAA
ATTAAATATTTTTTTTAATACATTTTCAATAACAAACACTTTAAAATATAATCTTTG
TCACACTCTTAAACAGTAACAGCAGAAAGCATATGTGAGTGATATAGCTATAGTTGC
TGTTTGACACGGACAATCTCCATCTAAATTCATGAATAATAAAGTTTTGCCTACACA
CCCACTTGAAATCTCCTCCTAGTTTTCCTGATTTGCCATGCTAACTACAAGAACAAG
ATGCTAGCTAGTATCTTGTTCTGTCTCTCGCTCTCTCTCTATCTCTCCAGTTGATAG
TTGATAGTTGATAGTTGATAGCTGATACCCTCCCACCTTTCCCAGAAAGATGATTGA
GGAACTAGTCACTGTGTTCGTGTAACTAATACTGTTCATGGCACCTAACTTGATCCT
CTCTTCACCAGACCACTATAAAAACCCTATCTGTCCTCCTCATAATCATATCACTAC
ACCCAACACTTCTGCAAGCACAACTCCATTCAAGAACATCAAGAGTATAGGCCGCCG
CTGCAACAAAACAGCACTCCTAGCTACTTCAAGATGAGGCCACAATCTTTCATCTT

Figure 12

Upstream genomic sequences (1236bp) of Poplar gene model estExt_Genewise1_v1.C_LG_IX4802.

TTCCCCCTTTTGGTTCAATGCCTTTTATTCTTCCAAATTAATTTCAATATTTTATAT
CCGGAGGAACATATTTGTTTCAAAAGGTGTCAGAAAATCAAAGCCCATTGAAAATAT
ATAAACATATATAGATATAAAAACTCAAGGATTCATTCCAAAATATAAGAACAAACT
GATTGAATTAATTTGTTATTTTAAGAACACTGTCTATATGTTTTTTTTTAGTTTAAC
GTGGGTGTCCGGGCCAGCTTGCGCGCACCTCAACTAATCCCACGGGTCCTGAAGTTA
ACGATCATGTAAGTCTCCAGTAGCCATCATATGAGCAACCACAGGGCTCGAACCTGA
GACCACAGAAGGAGCAAACCTCTTGGTCCCAAACTCTTACCATTGAGCTACCATCTA
GATGGTTACACTGTCTATATATTTATATAGTGGTAGGTAGTGTTTTTAAAATCATAT
ACTAACTTATTATAAAAATAAATCATAAAAAAGGAACCTCAAGCATCCCTTTGTAAG
CTCGTATGTAGGAATACTCGGAGATCAAATGTCCGAATGTCAAATGTTAAGGCAAGT
GAAATATCCCTAACTTTTTAGCAAGCAAATTGTTGAGTAGCTAAAATGAATTATTTT
AATATTTTTAAATCATTTTAATATATTAATATTAAAAAAAATTAAATATTTTTTTTA
ATACATTTTCAATAACAAACACTTTAAAATATAATCTTTGTCACACTCTTAAACAGT
AACAGCAGAAAGCATATGTGAGTGATATAGCTATAGTTGCTGTTTGACACGGACAAT
CTCCATCTAAATTCATGAATAATAAAGTTTTGCCTACACACCCACTTGAAATCTCCT
CCTAGTTTTCCTGATTTGCCATGCTAACTACAAGAACAAGATGCTAGCTAGTATCTT
GTTCTGTCTCTCGCTCTCTCTCTATCTCTCCAGTTGATAGTTGATAGTTGATAGTTG
ATAGCTGATACACTCCCACCTTTCCCAGAAAGATGATTGAGGAACTAGTCACTGTGT
TCGTGTAACTAATACTGTTCATGGCACCTAACTTGATCCTCTCTTCACCAGACCACT
ATAAAAACCCTATCTGTCCTCCTCATAATCATCTCACTACACCCAACACTTCTGCAA
GCACAACTCCATTCAAGAACATCAAGAGTATAGGCCGCCACTGCAACAAAACAGCAC
TCCTAGCTACTTCAAGATGAGGCCACAATCTTTCATCTT

COMPOSITIONS AND METHODS FOR XYLEM-SPECIFIC EXPRESSION IN PLANT CELLS

PRIORITY CLAIM TO RELATED APPLICATIONS

This application is a U.S. National Stage Filing under 35 U.S.C. §371 of International Patent Application Serial No. PCT/US2011/051371, filed Sep. 13, 2011, and published on Mar. 22, 2012 as WO 2012/037107, which claims priority under 35 U.S.C. §119 to U.S. Provisional Application Ser. No. 61/382,734, filed Sep. 14, 2010, the disclosures of which applications are specifically incorporated herein by reference in their entireties.

This invention was made with government support under grant No. DE-FC02-07ER64494 awarded by the Department of Energy, Great Lakes Bioenergy Research Center (DOE-GLBRC). The government has certain rights in the invention.

FIELD OF INVENTION

The invention provides promoter sequences that regulate specific expression of operably linked sequences in developing xylem cells and/or in developing xylem tissue. The developing xylem-specific sequences are exemplified by the DX5, DX8, DX11, and DX15 promoters, portions thereof, and homologs thereof. The invention further provides expression vectors, cells, tissues and plants that contain the invention's sequences. The compositions of the invention and methods of using them are useful in, for example, improving the quantity (biomass) and/or the quality (wood density, lignin content, sugar content etc.) of expressed biomass feedstock products that may be used for bioenergy, biorefinary, and generating wood products such as pulp, paper, and solid wood.

BACKGROUND

The successful application of biotechnology in crop and plant management and/or improvement is based on the discovery of novel genes and proper means for the control of their expression in resulting transgenic crops. However, commercial use of biotechnology in crop improvement programs is severely hindered by the lack of promoters that can drive gene expression in a tissue-specific and/or or temporally controlled manner. Although there have been reports of inducible promoters in plant biology literature, nonetheless, there are no reports in the art to-date regarding developing xylem cell-specific and/or developing xylem tissue-specific promoters.

Thus there is a need for promoters that are specific for expression in developing xylem cells and/or in developing xylem tissue.

SUMMARY OF THE INVENTION

The invention provides promoter sequences that regulate expression of operably linked sequences in developing xylem cells and/or in developing xylem tissue. The developing xylem promoter sequences are exemplified by the DX5, DX8, DX11, and DX15 promoters, portions thereof, and homologs thereof. The invention further provides expression vectors, cells, tissues and plants that contain the invention's sequences. The compositions of the invention and methods of using them are useful in, for example, improving the quantity (biomass) and/or the quality (wood density, lignin content, sugar content etc.) of expressed biomass feedstock products that may be used for bioenergy, biorefinary, and generating wood products such as pulp, paper, and solid wood.

Thus, in one embodiment, the invention provides an isolated nucleic acid sequence comprising a sequence selected from the group of a) a promoter sequence selected from the group of DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08, and b) a portion of a the promoter sequence, wherein the portion has promoter activity, and c) a sequence homologous to the promoter sequence, wherein the homologous sequence has i) at least 95% identity to the promoter sequence, and ii) promoter activity. In one embodiment, the promoter sequence drives developing xylem-specific expression of an operably-linked second nucleic acid sequence in a plant cell. In an alternative embodiment, the second nucleic acid sequence encodes a sequence selected from the group of (a) polypeptide involved in biosynthesis of a polysaccharide selected from cellulose and lignin, (b) antisense RNA of a sequence involved in biosynthesis of a polysaccharide selected from cellulose and lignin, and (c) interference RNA (iRNA) such as small interference RNA (siRNA) of a sequence involved in biosynthesis of a polysaccharide selected from cellulose and lignin. In a further embodiment, the portion comprises at least 100 nucleotides.

The invention further provides an expression vector comprising any one or more of the nucleic acid sequences described herein, and in particular, comprising a nucleic acid sequence comprising a sequence selected from the group of a) a promoter sequence selected from the group of DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08, and b) a portion of a the promoter sequence, wherein the portion has promoter activity, and c) a sequence homologous to the promoter sequence, wherein the homologous sequence has i) at least 95% identity to the promoter sequence, and ii) promoter activity.

The invention additionally provides a cell comprising one or more heterologous nucleic acid sequence as described herein, and in particular, comprising a nucleic acid sequence comprising a sequence selected from the group of a) a promoter sequence selected from the group of DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08, and b) a portion of a the promoter sequence, wherein the portion has promoter activity, and c) a sequence homologous to the promoter sequence, wherein the homologous sequence has i) at least 95% identity to the promoter sequence, and ii) promoter activity. In one embodiment, the cell is selected from the group of bacterial cell, mammalian cell, insect cell, plant cell, and fungal cell. In a further embodiment, the plant cell is selected from the group of developing xylem cell and seed cell.

Also provided herein is a transgenic plant comprising any one or more nucleic acid sequence described herein, wherein the nucleic acid sequence is operably linked to a heterologous second nucleic acid sequence, and in particular, wherein the nucleic acid sequence comprises a sequence selected from the group of a) a promoter sequence selected from the group of DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08, and b) a portion of a the promoter sequence, wherein the portion has promoter activity, and c) a sequence homologous to the promoter sequence, wherein the homologous sequence has i) at least 95% identity to the promoter sequence, and ii) promoter activity. In one embodiment, the second nucleic acid sequence encodes a sequence selected from the group of (a) polypeptide involved in biosynthesis of a polysaccharide selected from cellulose and lignin, (b) antisense RNA of a sequence involved in biosynthesis of a polysaccharide selected from cellulose and lignin, and (c) interference RNA (iRNA) such as small interference RNA (siRNA) of a sequence involved in biosynthesis of a polysaccharide selected from cellulose and lignin.

The invention also provides a seed produced by any one or more of the transgenic plants described herein.

Also provided by the invention is a composition comprising xylem, wherein the xylem is produced by any one or more of the transgenic plants described herein.

The invention also provides a method for expressing a nucleotide sequence in a plant cell, comprising a) providing i) any one or more of the nucleic acid sequences described herein, and in particular, a first nucleic acid sequence comprising a sequence selected from the group of a) a promoter sequence selected from the group of DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08, and b) a portion of a the promoter sequence, wherein the portion has promoter activity, and c) a sequence homologous to the promoter sequence, wherein the homologous sequence has i) at least 95% identity to the promoter sequence, and ii) promoter activity, and wherein the first nucleic acid sequence is operably linked to a second nucleotide sequence, and ii) plant cell, b) introducing the nucleic acid sequence into the plant cell to produce a transgenic plant cell, wherein the introducing is under conditions for expression of the second nucleic acid sequence in the transgenic cell. In one embodiment, the method further comprises c) detecting expression of the second nucleic acid sequence in the transgenic cell. In an alternative embodiment, the second nucleic acid sequence encodes a sequence selected from the group of (a) polypeptide involved in biosynthesis of a polysaccharide selected from cellulose and lignin, (b) antisense RNA of a sequence involved in biosynthesis of a polysaccharide selected from cellulose and lignin, and (c) interference RNA (iRNA) such as small interference RNA (siRNA) of a sequence involved in biosynthesis of a polysaccharide selected from cellulose and lignin. In yet another embodiment, the method further comprises c) regenerating a transgenic plant from the transgenic plant cell. In a further embodiment, the method further comprises d) detecting expression of the second nucleic acid sequence in a developing xylem cell of the transgenic plant. In an additional embodiment, the expression is developing xylem-specific expression.

BRIEF DESCRIPTION OF THE DRAWINGS

FIG. 1. Sampling scheme for tissue-specific whole transcriptome analysis.

FIG. 2. Principal component analysis.

FIG. 3. Validation of GeneChip data by using cell-type specific marker.

FIG. 4. Identification of developing xylem (DX) specific genes.

FIG. 5. Confirmation of developing xylem-specific expression of selected genes by using semi-quantitative RT-PCR.

FIG. 6. Developing xylem-specific GUS gene expression driven by promoters of both PtrNAC073 (X5) and ANAC073 in poplar plants.

FIG. 7. Upstream genomic sequence (1941 bp) (SEQ ID NO:01) of the poplar plant gene model estExt_fgenesh4_pg.C_640203. The underlined upstream sequence comprises the DX5 promoter (SEQ ID NO:02), which is upstream of the coding sequence that begins with ATG.

FIG. 8. Upstream genomic sequence (1517 bp) (SEQ ID NO:03) of the poplar plant gene model eugene3.02290017. The underlined upstream sequence comprises the DX8 promoter (SEQ ID NO:04), which is upstream of the coding sequence that begins with ATG.

FIG. 9. Upstream genomic sequence (1315 bp) (SEQ ID NO:05) of the poplar plant gene model estExt_Genewise1_v1.C_LG_III1078. The underlined upstream sequence comprises the DX11 promoter (SEQ ID NO:06), which is upstream of the coding sequence that begins with ATG.

FIG. 11. Upstream genomic sequence (1025 bp) (SEQ ID NO:07) comprising the DX15 promoter sequence (SEQ ID NO:08), which is underlined, and which is upstream of the coding sequence that begins with ATG.

FIG. 12. Upstream genomic sequence (1236 bp) (SEQ ID NO:09) of the poplar plant gene model estExt_Genewise1_v1.C_LG_IX4802, as listed on the world-wide web. The underlined promoter sequence (SEQ ID NO:10), which is upstream of ATG, is different from the DX15 promoter sequence (SEQ ID NO:08) of FIG. 11.

DEFINITIONS

Figure 10:
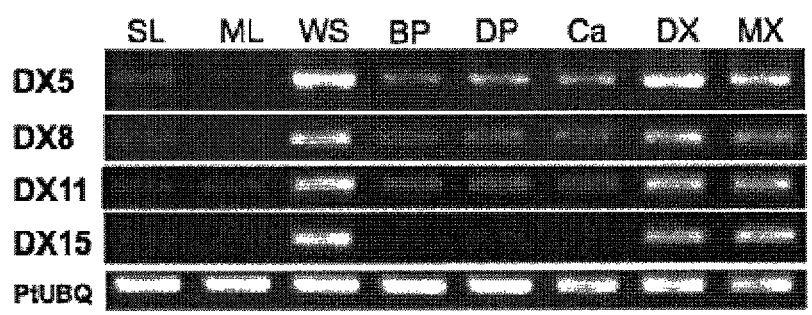
FIG. 10. Developing xylem-specific expression of selected genes under control of DX5, DX8, DX11, and DX15 promoter sequences using RT-PCR. Conditions for RT-PCR: volume=10 µl, annealing Tm=53, Extenion=30 seconds, Cycles=28, Template=cDNA from poplar. SL: SAM+LP. ML: Matrue Leaf. WS: Whole stem. BP: Bark & phloem. DP: Developing phloem. Ca: Cambium. DX: Developing xylem. MX: Mature Xylem.

To facilitate understanding of the invention, a number of terms are defined below.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed using a recombinant DNA molecule.

The term "promoter," "promoter element," or "promoter sequence" as used herein, refers to a DNA sequence which when ligated to a nucleotide sequence of interest is capable of controlling the transcription of the nucleotide sequence of interest into mRNA. The terms "control," "drive," "regulate," and "facilitate" when used in reference to a promoter are interchangeably used to refer to the activity of the promoter in bringing about and/or altering the level of transcription of an operably linked sequence. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Sequence "identity" when in reference to two or more sequences (e.g., DNA, RNA, and/or protein sequences) refers to the residues in the two sequences that are the same when the two sequences are aligned for maximum correspondence over a specified region. Identity is generally expressed as a percentage. The percentage is calculated by determining the number of positions at which identical residues (i.e., nucleic acid bases in DNA and RNA, and amino acids in proteins) occur in both aligned sequences to yield the number of matched positions, dividing the number of matched positions by the total number of positions in the region of comparison, and multiplying the result by 100 to yield the percentage of sequence identity. Identity in amino acid or nucleotide sequences can be determined using Karlin and Altschul's BLAST algorithm (Proc. Natl. Acad. Sci. USA, 1990, 87, 2264-2268; Karlin, S. & Altschul, S F., Proc. Natl. Acad. Sci. USA, 1993, 90, 5873). Programs called BLASTN and BLASTX have been developed using the BLAST algorithm as a base (Altschul, S F. et al., J. Mol. Biol., 1990, 215, 403). When using BLASTN to analyze nucleotide sequences, the parameters can be set at, for example, score=100 and word length=12. In addition, when using BLASTX to analyze amino acid sequences, the parameters can be set at, for example, score=50 and word length=3. When using BLAST and the Gapped BLAST program, the default parameters for each program are used. Specific techniques for these analysis methods are the well known, e.g., on the website of the National Center for Biotechnology Information The terms "mutation" and "modification" refer to a deletion, insertion, or substitution.

A "deletion" is defined as a change in a nucleic acid sequence or amino acid sequence in which one or more nucleotides or amino acids, respectively, is absent.

An "insertion" or "addition" is that change in a nucleic acid sequence or amino acid sequence that has resulted in the addition of one or more nucleotides or amino acids, respectively.

A "substitution" in a nucleic acid sequence or an amino acid sequence results from the replacement of one or more nucleotides or amino acids, respectively, by a molecule that is a different molecule from the replaced one or more nucleotides or amino acids. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. Substitution of an amino acid may be conservative or non-conservative. "Conservative substitution" of an amino acid refers to the replacement of that amino acid with another amino acid that has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains that may be conservatively substituted one for the other include phenylalanine, tyrosine, and tryptophan. Cysteine and methionine are sulphur-containing amino acids that may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. "Non-conservative substitution" is a substitution other than a conservative substitution. Guidance in determining which and how many amino acid residues may be substituted, inserted or deleted without abolishing biological and/or immunological activity may be found using computer programs well known in the art, for example, DNAStar™ software.

The term "recombinant mutation" refers to a mutation that is introduced by means of molecular biological techniques. This is in contrast to mutations that occur in nature.

"High stringency conditions" when used in reference to hybridization of nucleic acid sequences comprise conditions equivalent to binding or hybridization at 42° C. in a solution of 5×SSPE (43.8 g/l NaCl, 6.9 g/l $NaH_2PO_4$—$H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed. In another embodiment, high stringency conditions comprise conditions equivalent to binding or hybridization at 68° C. in a solution containing 5×SSPE, 1% SDS, 5×Denhardt's reagent and 100 µg/ml denatured salmon sperm DNA followed by washing in a solution containing 0.1×SSPE, and 0.1% SDS at 68° C.

A peptide sequence and nucleotide sequence may be "endogenous" or "heterologous" (i.e., "foreign"). The terms "endogenous" and "wild type" refer to a sequence that is naturally found in the cell or virus. Thus, an endogenous sequence may be introduced into a cell or virus so long as it does not contain some modification relative to the naturally occurring sequence. The tetra "heterologous" refers to a sequence that is not endogenous to the cell or virus. For example, heterologous DNA includes a nucleotide sequence that is ligated to, or is manipulated to become ligated to, a nucleic acid sequence to which it is not ligated in nature, or to which it is ligated at a different location in nature. Heterologous DNA also includes a nucleotide sequence that is naturally found in the cell or virus into which it is introduced and which contains some modification relative to the naturally occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc.

The term "transgenic" when used in reference to a cell refers to a cell which contains a transgene, or whose genome has been altered by the introduction of a "transgene" i.e., any nucleic acid sequence which is introduced into the cell by experimental manipulations.

The terms "purified" and "isolated" and grammatical equivalents thereof as used herein, refer to the reduction in the amount of at least one undesirable contaminant (such as protein and/or nucleic acid sequence) from a sample. Thus, purification results in an "enrichment," i.e., an increase in the amount of a desirable composition, such as a virus, protein and/or nucleic acid sequence in the sample. For example, wood and wood pulp that are produced by cells that have been transformed by the invention's sequences may be purified using methods known in the art.

The terms "operable combination" and "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest resulting in an mRNA that directs the synthesis of a polypeptide encoded by the nucleotide sequence of interest.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. Methods for designing and using ribozymes are known (e.g., Wagner et al. U.S. Pat. No. 6,355,415, hereby incorporated by reference). "Antisense inhibition" refers to the production of antisense RNA transcripts capable of preventing the expression of the target protein.

The term "interference RNA" or "iRNA" refers to RNA used in the silencing or decreasing of gene expression. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. iRNA may also be considered to inhibit the function of a target RNA; the function of the target RNA may be complete or partial.

The term "siRNAs" refers to "short interfering RNAs." In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, which link the two strands of the double strand, as well as stem and other folded structures, which may be present within the linking sequence. siRNAs appear to function as key intermediaries in triggering RNA interference in invertebrates and in vertebrates, and in triggering sequence-specific RNA degradation during posttranscriptional gene silencing in plants.

The term "plant" as used herein refers to a plurality of cells from a photosynthetic, eukaryotic, multicellular organism of the kingdom Plantae, characteristically producing embryos, containing chloroplasts, and having cellulose cell walls, wherein the cells are largely differentiated into a structure that is present at any stage of a plant's development. Such structures include, but are not limited to, a fruit, shoot, stem, leaf, flower petal, etc. In particular embodiments, the plant is a woody plant. Plants include angiosperm plants (including monocotyledonous plants and dicotyledenous plants) and gymnosperm plants.

"Plant cell" is the structural and physiological unit of plants, consisting of a protoplast and the cell wall, and may be derived from a plant, plantlet, seed, tissue, organ, callus, protocorm-like body, suspension culture, protoplasts, and the like. "Plant cell suspension culture" refers to plant cells in liquid medium.

"Plant tissue" is a plurality of plant cells organized into a structural and functional unit. "Plant tissue" includes differentiated and undifferentiated tissues, such as, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, cell culture, etc.

"Plant organ" is a collection of tissues that performs a particular function or set of functions in a plant's body. The leaf, stem, and root are exemplary organs found in many plants. Organs are composed of tissues.

The term "totipotent body" as used herein refers to a collection of cells (e.g., a cell aggregate) comprising undifferentiated plant cells capable of differentiation into a plant. A totipotent body may also contain some differentiated cells. A "totipotent body" includes, but is not limited to, a protocorm-like body, a callus, and the like. The ability of a totipotent body to differentiate into a plant is determined using methods known in the art as well as methods described herein. For example, differentiation into shoots may be accomplished by culturing a totipotent body on agar-solidified hormone-free modified MS medium, or on agar-solidified PM2 medium. Differentiation into roots may be accomplished by culture of a totipotent body in liquid modified MS medium containing 1 mg/L NAA.

"Plant callus" is a cluster of undifferentiated plant cells that have the capacity to regenerate a whole plant.

"Protocorm-like body," "plb," and "nodular body" when made in reference to pineapple refer to a totipotent body which is generally, though not necessarily, creamy yellow and globular shaped. A plb derived form pineapple tissue is morphologically distinguishable from a callus derived from pineapple. For example, a plb that is derived from pineapple tissue is characterized by having a partially organized morphology with a pre-determined apical meristematic region covered by a distinctive epidermal layer but lacking vascular tissue; a callus derived from pineapple tissue is a disorganized mass of undifferentiated plant cells lacking apical meristem, epidermis, and vascular tissue. Additionally, in vitro culture conditions for the generation of a plb are different from those for the generation of a callus. For example, pineapple plbs may be generated as previously described (Wakasa et al. (1978) Japan. J. Breed. 28:113-121, Mapes (1973) Proc. Intl. Plant Propagation Soc. 23:47-55) and using methods described herein. Pineapple callus may be produced as described by (Mathews et al., (1981) Scientia Horiculturae 14:227-234).

The term "embryonic cell" as used herein in reference to a plant cell refers to a plant cell (whether differentiated or un-differentiated) that is capable of differentiation into a plant tissue or plant. Embryonic cells include, without limitation, protoplasts such as those derived from the genera

*Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*. Also included are embryos such as those from sorghum, from maize (U.S. Pat. No. 5,593,874), and from banana, embryonic meristems such as those from soybean (U.S. Pat. No. 5,015,580), embryogenic callus such as from sugarcane, protocorm-like bodies such as from pineapple, and embryogenic cells as exemplified by those from garlic. The ability of an embryonic cell to differentiate into a plant is determined using methods known in the art as well as methods described herein. For example, differentiation of pineapple protocorm-like bodies into shoots may be accomplished by culturing the protocorm-like body on agar-solidified hormone-free modified Murashige & Skoog (MS) medium or on agar-solidified PM2 medium (U.S. Pat. No. 6,091,003). Differentiation into pineapple roots may be accomplished by culture of protocorm-like bodies in liquid modified MS medium containing 1 mg/L NAA.

"xylem" is a plant tissue that includes more than one type of cell, including the tracheary elements (tracheids and vessel elements), parenchyma, etc. Xylem's primary function is the transport of water and soluble mineral nutrients from the roots throughout the plant. Xylem is found throughout the plant, such as wood. Wood (i.e., lignocellulose) is increasingly becoming a more valuable raw material not only for its traditional uses (e.g., raw materials for furniture, construction, paper industry) but also as a source of fermentable sugars for liquid fuel production, as a feedstock, etc. Wood biomass is composed of a complex mixture of cellulose, hemicellulose, and lignin. Wood is formed as a result of the successive addition of the secondary xylem after differentiation of the developing xylem (DX) cells, which locate on the xylem side of the vascular cambium. Xylem is also found in vascular bundles (present in non-woody plants and non-woody parts of plants with wood), in secondary xylem that is laid down by a meristem called the vascular cambium in woody plants, and as part of a stellar arrangement not divided into bundles, as in many ferns. Xylem includes developing xylem and mature xylem.

"Developing xylem" and "primary xylem" interchangeably refer to the xylem that is formed during primary growth from procambium. It includes protoxylem and metaxylem. Metaxylem develops after the protoxylem but before mature xylem. It is distinguished by wider vessels and tracheids. As it develops, the developing xylem can become endarch or exarch. Developing xylem is found in woody plants, including hardwood plants (e.g., dicotyledenous angiospethis), and softwood plants (e.g., gymnosperms).

"Mature xylem" and "secondary xylem" interchangeably refer to xylem that is formed during secondary growth from vascular cambium. Mature xylem is found in conifers, angiosperms, and the gymnosperm groups Gnetophyta, Ginkgophyta, and Cycadophyta. Many conifers become tall trees, and the mature xylem of such trees is marketed as softwood. Within angiosperms, mature xylem has not been found in the monocots. Many non-monocot angiosperms become trees, and the mature xylem of these is marketed as hardwood.

"Lignin" refers to a polymeric composition composed of phenylpropanoid units, including polymerized derivatives of monolignols coniferyl, coumaryl, and sinapyl alcohol. Lignin quality refers to the ability of a lignin composition to impart strength to cell wall matrices, assist in the transport of water, and/or impede degradation of cell wall polysaccharides. Lignin composition or lignin structure may be changed by altering the relative amounts of monolignols and/or by altering the type of lignin. For example, guaiacyl lignins (derived from ferulic acid) are prominent in softwood species, whereas guaiacyl-syringyl lignins (derived from ferulic acid and sinapic acid) are characteristic of hardwood species. TLignin composition may be regulated by either up-regulation or down-regulation of enzymes involved lignin biosynthesis, such as those involved in 4-coumaric acid synthesis: coenzyme A ligase (4CL), Cinnamyl Alcohol dehydrogenase (CAD), and Sinapyl Alcohol Dehydrogenase (SAD).

"Wood composition" and "fiber composition" refer to a trait that can be modified to change the structure and/or appearance of wood. Such traits include but are not limited to wood fiber length, coarseness, strength, color, cross-section, width, and density. For example, fiber length imparts strength, whereas fiber coarseness determines texture and flexibility. These traits may alter cell wall thickness, cell length, cell size, lumen size, cell density, microfibril angle, tensile strength, tear strength, wood color, and/or frequency of cell division.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, etc.), cell, and/or phenomenon (e.g., disease resistance, environmental stress tolerance, binding to a molecule, specificity of binding of two molecules, affinity of binding of two molecules, enzyme activity, etc.) in a first sample relative to a second sample, mean that the quantity of molecule, cell and/or phenomenon in the first sample is lower than in the second sample by any amount that is statistically significant using any art-accepted statistical method of analysis. In one embodiment, the quantity of molecule, cell and/or phenomenon in the first sample is at least 10% lower than, at least 25% lower than, at least 50% lower than, at least 75% lower than, and/or at least 90% lower than the quantity of the same molecule, cell and/or phenomenon in the second sample. In another embodiment, the quantity of molecule, cell, and/or phenomenon in the first sample is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample The terms "increase," "elevate," "raise," and grammatical equivalents (including "higher," "greater," etc.) when in reference to the level of any molecule (e.g., amino acid sequence, and nucleic acid sequence, etc.), cell, and/or phenomenon (e.g., disease resistance, environmental stress tolerance, binding to a molecule, specificity of binding of two molecules, affinity of binding of two molecules, enzyme activity, etc.) in a first sample relative to a second sample, mean that the quantity of the molecule, cell and/or phenomenon in the first sample is higher than in the second sample by any amount that is statistically significant using any art-accepted statistical method of analysis. In one embodiment, the quantity of the molecule, cell and/or phenomenon in the first sample is at least 10% greater than, at least 25% greater than, at least 50% greater than, at least 75% greater than, and/or at least 90% greater than the quantity of the same molecule, cell and/or phenomenon in the second sample. This includes, without limitation, a quantity of molecule, cell, and/or phenomenon in the first sample that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample.

The terms "alter" and "modify" when in reference to the level of any molecule and/or phenomenon refer to an increase or decrease.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

DESCRIPTION OF THE INVENTION

The invention provides the discovery of genes from poplar plants, which are specifically and strongly expressed in xylem cells and xylem tissue, and in particular are specifically expressed in developing xylem cells and developing xylem tissue. These genes were discovered by analysis of the Poplar Genome Array (Affymetrix).

In order to identify specifically and strongly expressed genes in developing xylem cells and/or developing xylem tissue of woody plants, the inventors generated the tissue type-specific transcriptomes from poplar stem tissues by using systematic analysis of Poplar Genome Array (Affymetrix). Bioinformatic analyses followed by the validation of tissue type-specific transcriptomes led to the identification of several genes specifically expressed in developing xylem cells and/or developing xylem tissue of poplar plants.

Thus, in one embodiment, the invention provides the discovery of developing xylem cell-specific promoters and/ or developing xylem tissue-specific promoters that are exemplified by DX5, DX8, DX11, and DX15 promoters. The use of these promoters for developing xylem cell-specific and/or developing xylem tissue-specific gene expression has been demonstrated in the exemplary transgenic poplar plants using the exemplary GUS reporter gene.

The developing xylem cell-specificity and/or developing xylem tissue-specificity of the compositions and methods of the invention have several advantages, including changing the phenotype of particular cells (e.g., developing xylem cells) to improve the quantity (biomass) and/or the quality (wood density, lignin content, sugar content etc.) of certain products, and cost reduction by producing engineered feedstock at a lower cost.

Thus, some of the uses of the invention's compositions and methods include biomass feedstock manipulation for bioenergy and biorefinary, and generating wood products such as pulp, paper, and solid wood for use as a building material and in the furniture industry, etc. In one embodiment, the invention's compositions and methods may be used for biomass feedstock manipulation, as exemplified by improving the rates and final yields of sugar release (saccharification potential) from woody biomass, by altering growth rate, flower development, root development, branching, seasonal responses such as light and cold controls on meristem identity, disease resistance, environmental stress tolerance, the yields of easily fermentable polysaccharides, cellulose synthesis, lignin deposition, total lignin content, lignin monomer composition, wood density, fiber composition, and lowering biomass recalcitrance to fermentation. For example, to facilitate making pulp from trees, the wood fibers may be made to separate more easily. To produce ethanol, the concentration of sugars in the feedstock may be increased using the invention's promoters. To increase wood strength, the amount of lignin in the wood can be increased, the wood will be stronger. Conversely, by reducing the lignin content in wood, it is easier to use the wood to produce sugars for ethanol production. By changing the hemicellulose content, the biomass will be better suited for use in the production of biofuel.

The invention is further described under A) Homologs and Portions Of the invention's developing xylem cell-specific and/or tissue specific promoters, B) Developing Xylem-Cell Specific and Developing Xylem-Tissue Specific Expression, C) Sequences Expressed under Control of The Invention's Promoter Sequences, D) Expression Vectors, E) Transgenic Cells, F) Transgenic Plants, G) Regeneration of Transgenic Plants A. Homologs and Portions of the Invention's Developing Xylem Cell-Specific and/or Tissue Specific Promoters The invention provides the DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08. However, the invention is nonetheless not limited to these particular sequences, but rather expressly contemplates portions and homologs of these sequences.

As used herein the term "portion" when made in reference to a nucleic acid sequence refers to a fragment of that sequence. The fragment may range in size from an exemplary 5, 10, 20, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, and 1,900 contiguous nucleotide residues to the entire nucleic acid sequence minus one nucleic acid residue. Thus, a nucleic acid sequence comprising "at least a portion of" a nucleotide sequence comprises from five (5) nucleotide residue of the nucleotide sequence to the entire nucleotide sequence. Functional portions of the invention's promoter sequences that have promoter activity may be determined using methods known in the arts, such as by sequential deletion of one or more nucleotides from the 5' and/or 3' end, coupled with the determination of the promoter activity of the resulting portion.

A "variant" or "homolog" of a polypeptide sequence of interest or nucleotide sequence of interest, refers to a sequence that has at least 80% identity, including 81%, 82%, 83%, 84%, 85%, 86%, 87%, 88%, 89%, 90%, 91%, 92%, 93%, 94%, 95%, 96%, 97%, 98%, and 99%, identity with the a polypeptide sequence of interest or nucleotide sequence of interest, respectively. Thus, in one embodiment, a homologous sequence refers to a sequence that contains a mutation relative to the sequence of interest. In another embodiment, the homologous nucleotide sequence refers to a sequence that hybridizes under stringent conditions to the nucleotide sequence of interest.

Thus, in one embodiment, a homolog of the DX5 promoter (SEQ ID NO:02) of the Poplar gene model estExt_fgenesh4 pg.C_640203 is exemplified by sequences from the *Arabidopsis* gene (At4g28500).

In another embodiment, a homolog of the DX8 promoter (SEQ ID NO:04) of the Poplar gene model eugene3.02290017 is exemplified by sequences from the *Arabidopsis* gene (At5g42710).

In a further embodiment, a homolog of the DX11 promoter (SEQ ID NO:06) of the Poplar gene model estExt_Genewise1_v1.C_LG_III1078 is exemplified by sequences from the *Arabidopsis* gene (At1g27920).

In another embodiment, a homolog of the DX15 promoter (SEQ ID NO:08) is exemplified by the sequences from the *Arabidopsis* gene (At5g60490).

B. Developing Xylem-Cell Specific and Developing Xylem-Tissue Specific Expression The invention's DX5, DX8, DX11, and DX15 promoter sequences, portions and homologs thereof, are xylem-specific, and in particular are developing xylem-specific. This specificity may be desirable to alter the quality and/or quantity of wood. Wood is formed as a result of the successive addition of the secondary xylem after differentiation of the developing xylem cells (DX), which locate on the xylem side of the vascular cambium.

"Xylem-specific" when in reference to a promoter activity means that expressing a second nucleic acid sequence that is operably linked to the promoter, results in a higher level of an expression product (e.g., RNA sequence and/or polypeptide that is encoded by the second nucleic acid sequence) in xylem tissue and/or xylem cell as compared to another plant tissue (e.g., leaf tissue, flower tissue, reproductive tissue, seed tissue, etc.) and/or plant cell (e.g., leaf cell, flower cell, reproductive cell, seed cell, etc.). Thus, in one embodiment, "xylem-specific" expression refers to a level of an expression product in xylem tissue and/or xylem cell that is at least 50% greater, at least 100% greater, at least 150% greater, at least 200% greater, at least 250% greater, at least 200% greater, at least 350% greater, at least 300% greater, at least 450% greater, at least 400% greater, at least 550% greater, at least 500% greater, at least 550% greater, at least 600% greater, at least 650% greater, at least 700% greater, at least 750% greater, at least 800% greater, at least 850% greater, at least 900% greater, at least 950% greater, and/or at least 1,000% greater, than the level of the expression product in another plant tissue.

This includes, but is not limited to, the presence of a detectable level of the expression product in plant xylem tissue and/or xylem cell, and the absence of detectable levels in another plant tissue.

Methods for xylem-specific gene expression in a plant cell are described herein. Generic methods for tissue-specific and/or cell-specific gene expression are also known in the art (Phillips et al., U.S. Pat. No. 7,365,186; a promoter from the region upstream of the 4CL gene in *Pinus taeda* that directs expression specifically to the xylem of Chiang et al., U.S. Pat. No. 6,252,135 and of Forster et al. U.S. Pat. No. 7,402,428; the bean grp 1.8 promoter, which is specifically active in protoxylem tracheary elements of vascular tissue of Keller et al., EMBO J. 8: 1309 (1989); the *Eucalyptus* CAD promoter that is preferentially expressed in lignifying zones of Feuillet et al., *Plant Mol. Biol.* 27: 651 (1995); Torres-Schumann S, al., "In Vitro Binding of the Tomato bZIP Transcriptional Activator VSF-1 to a Regulatory Element that Controls Xylem-Specific Gene Expression", The Plant Journal, 1996, vol. 9, No. 3, pp. 283-296; and No E G et al., "Sequences Upstream and Downstream of Two Xylem-Specific Pine Genes Influence Their Expression", Plant Science, 2000 Elsevier Science, vol. 160, pp. 77-86.

For example, data herein demonstrate that the invention's promoters are not only highly specific to DX, but also produced high level expression in DX (Example 3, FIGS. 4, 5 and 10).

Also, data herein show that the invention's promoter sequences produced expression of the exemplary gus gene in xylem cells of stems, in the substantial absence of expression in leaf tissue (Example 4, FIG. 6). Gene expression under the control of the PtrNAC073 promoter (FIG. 6A) and the ANAC073 promoter (FIG. 6B) was specifically observed in the developing xylem cells of the stem (FIG. 6A), with no expression in leaf tissue. Further xylem-specific expression under control of DX5, DX8, DX11, and DX15 promoter sequences is shown in FIG. 10.

C. Sequences Expressed Under Control of the Invention's Promoter Sequences

The invention's DX5, DX8, DX11, and DX15 promoter sequences, portions and homologs thereof, may be operably linked to second nucleic acid sequence to bring about developing xylem-cell specific and/r developing xylem-tissue specific expression of the second nucleic acid sequence.

Without intending to limit the type or source of the second nucleic acid sequence, in one embodiment, the second nucleic acid sequence encodes (a) a polypeptide involved in biosynthesis of a polysaccharide such as cellulose, hemicellulose, and lignin (b) antisense RNA of a sequence involved in biosynthesis of a polysaccharide such as cellulose, hemicellulose, and lignin, and (c) interference RNA (iRNA), such as small interference RNA (siRNA), of a sequence involved in biosynthesis of a polysaccharide such as cellulose, hemicellulose, and lignin.

Thus, in one embodiment, the second nucleic acid sequence encodes a polypeptide involved in biosynthesis of a polysaccharide such as cellulose, hemicellulose, and lignin. This may be desirable to increase expression of targeted genes. Polynucleotides encoding many of the enzymes involved in lignin biosynthesis are known and include, but are not limited to, cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate: CoA ligase (4CL) and peroxidase (PDX) from pine. U.S. Pat. No. 6,204,434. Other enzymes include coniferin β-glucosidase (CBG), Sinapyl Alcohol Dehydrogenase (SAD), and caffeic acid 3-O-methyltransferase (COMT). U.S. Pat. No. 5,451,514, WO 94/23044, and Dharmawardhana et al., Plant Mol. Biol. 40: 365-72 (1999).

In an alternative embodiment, the second nucleic acid sequence encodes antisense RNA of a sequence involved in biosynthesis of a polysaccharide such as cellulose, hemicellulose, and lignin. This may be desirable fir inhibiting expression of targeted genes. Thus, in one embodiment, the polynucleotide sequence of the present invention is operably linked to a coding sequence that reduces the expression and/or activity of an enzyme involved in lignin biosynthesis, such as an antisense gene encoding 4-coumarate:CoA ligase (4CL), cinnamyl alcohol dehydrogenase (CAD), and/or caffeic acid/5-hydroxyferulic acid O-methyltransferase (COMT).

Generic methods for using antisense technology to reduce or inhibit the expression of specific plant genes have been described (European Patent Publication No. 271988). Reduction of gene expression led to a change in the phenotype of the plant, either at the level of gross visible phenotypic difference, for example a lack of lycopene synthesis in the fruit of tomato leading to the production of yellow rather than red fruit, or at a biochemical level, for example, a change in the amount of polygalacturonase and reduction in depolymerization of pectins during tomato fruit ripening (Smith et. al., Nature, 334:724-726 (1988); Smith et. al., Plant Mol. Biol., 14:369-379 (1990)). Thus, antisense RNA has been demonstrated to be useful in achieving reduction of gene expression in plants.

In a particular embodiment, the second nucleic acid sequence encodes interfering RNA (iRNA), such as short interfering RNA (siRNA), which corresponds to a gene of interest, resulting in a decreased expression of targeted gene products. For example, the gene products targeted for suppression may be enzymes involved in lignin biosynthesis, such as 4-coumarate:CoA ligase (4CL), cinnamyl alcohol dehydrogenase (CAD), and/or caffeic acid/5-hydroxyferulic acid O-methyltransferase (COMT).

The use of iRNA inhibition of gene expression is described in U.S. Pat. No. 6,506,559, and the use of iRNA to inhibit gene expression in plants is specifically described in WO 99/61631.

D. Expression Vectors

The invention provides expression vectors comprising the invention's DX5, DX8, DX11, and DX15 promoter sequences, portions and homologs thereof, operably linked to a second nucleic acid sequence so as to result in expression of the second nucleic acid sequence.

The term "expression vector" as used herein refers to a recombinant DNA molecule containing a desired coding sequence and appropriate nucleic acid sequences necessary for the expression (i.e., transcription and/or translation) of the operably linked coding sequence in a particular host organism. Expression vectors are exemplified by, but not limited to, plasmid (including "bacterial artificial chromosomes," phagemid, shuttle vector, cosmid, virus, chromosome, mitochondrial DNA, plastid DNA, derivatives of plant tumor sequences, T-DNA sequences, and nucleic acid fragment. Expression vectors include "eukaryotic vectors," i.e., vectors that are capable of replicating in a eukaryotic cell (e.g., plant cell, yeast cell, mammalian cells, etc.) and "prokaryotic vectors," i.e., vectors that are capable of replicating in a prokaryotic cell (e.g., *E. coli*). Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals.

Large numbers of suitable vectors that function is prokaryotic, eukaryotic cells, and insect cells are known to those of skill in the art, and are commercially available. Prokaryotic bacterial vectors are exemplified by pBR322, pUC, pYeDP60, pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia). Eukaryotic vectors are exemplified by pMLBART, pSV2CAT, pOG44, PXT1, pSG (Stratagene) pSVK3, pBPV, pMSG, pSVL (Pharmacia), pGEMTeasy plasmid, pCambia1302 (for plant cell transformation using the exemplary *Agrobacteria tumefaciens* strain GV3101), and transcription-translation (TNT®) coupled wheat germ extract systems (Promega). Baculovirus vectors for expression in insect cells are also commercially available (e.g., Invitrogen). Any other vector may be used as long as it is replicable in the host.

Expression vectors contemplated within the scope of the invention include plant vectors. Plant expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences for expression in plants. In other embodiments, DNA sequences derived from the SV40 splice, and polyadenylation sites may be used to provide the required non-transcribed genetic elements.

Numerous transformation vectors are available for plant transformation (see U.S. Pat. Nos. 7,365,182 and 7,446,188, hereby incorporated by reference). The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18: 1062; Spencer et al. (1990) Theor. Appl. Genet. 79: 625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an *Agrobacterium* mediated transfection process (See for example, U.S. Pat. Nos. 5,981,839; 6,051,757; 5,981, 840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by

*Agrobacterium* transfer-DNA 1-DNA) sequences, as previously described (U.S. Pat. No. 5,501,967, hereby incorporated by reference). One of skill in the art knows that homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Generally, the inserted polynucleotide of the present invention can be expressed from these vectors as a fusion protein (for example, coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785.

In some embodiments of the present invention, the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

Further description is provided under a) Cell Transformation and b) Transformation Techniques.

a. Cell Transformation

The vectors of the invention may be introduced into cells using techniques well known in the art to produce a transformed cell. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus.

The terms "transform" and "transfect" as used herein, interchangeably refer to any mechanism by which a vector may be incorporated into a host cell. A successful transfection results in the capability of the host cell to express any operative genes carried by the vector.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA), which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell that has transiently incorporated one or more nucleotide sequences of interest.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the cell with nucleic acid sequences that are capable of binding to one or more of the nucleotide sequences of interest. Alternatively, stable transformation of a cell may also be detected by the polymerase chain reaction of genomic DNA of the cell to amplify the nucleotide sequence of interest.

b. Transformation Techniques

With respect to "plant expression vectors," i.e., vectors that are capable of replicating in a plant cell, transformation of a plant cell may be accomplished by a variety of means known in the art including particle mediated gene transfer (see, e.g., U.S. Pat. No. 5,584,807); infection with an *Agrobacterium* strain containing the foreign DNA for random integration (U.S. Pat. No. 4,940,838) or targeted integration (U.S. Pat. No. 5,501,967) of the foreign DNA into the plant cell genome; electroinjection; fusion with liposomes, lysosomes, cells, minicells or other fusible lipid-surfaced bodies; chemicals that increase free DNA uptake; transformation using virus, and the like.

Further, the invention's sequences may be introduced using direct transformation in the plastid genome (U.S. Pat. Nos. 5,451,513; 5,545,817; 5,545,818; PCT application WO 95/16783), microinjected directly into plant cells by use of micropipettes (Crossway (1985) Mol. Gen. Genet, 202:179), using polyethylene glycol (Krens et al. (1982) Nature, 296:72; Crossway et al. (1986) BioTechniques, 4:320), fusion of protoplasts with minicells, with cells, with lysosomes an/or or other fusible lipid-surfaced bodies (Fraley et al. (1982) Proc. Natl. Acad. Sci., USA, 79:1859), protoplast transformation (EP 0 292 435), direct gene transfer (Paszkowski et al. (1984) EMBO J., 3:2717; Hayashimoto et al. (1990) Plant Physiol. 93:857), electroporation. (Fromm, et al. (1985) Pro. Natl Acad. Sci. USA 82:5824; Riggs et al. (1986) Proc. Natl. Acad. Sci. USA 83:5602), ballistic particle acceleration (U.S. Pat. No. 4,945,050; McCabe et al. (1988) Biotechnology 6:923), Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al.

(1993) Plant Physiol., 102:1077 (wheat); Chang et al., WO 94/13822 (wheat) and Nehra et al. (1994) The Plant Journal, 5:285 (wheat), as well as using *Agrobacterium*-mediated transformation (Ishida et al. (1996) Nature Biotechnology 14:745). See also U.S. Pat. Nos. 7,365,182 and 7,446,188.

E. Transgenic Cells

The invention provides transgenic cells comprising the invention's DX5, DX8, DX11, and DX15 promoter sequences, portions and homologs thereof. The term "cell" refers to a single cell that may be comprised in a population of cells in vitro and/or in vivo.

Any type of cell into which the invention's vectors may be introduced is expressly included within the scope of this invention, including "eukaryotic cell" and "prokaryotic cell.

"Prokaryotic cell" includes bacteria, virus (including bacteriophage), blue-green algae, archaebacteria, actinomycetes and mycoplasma etc.).

"Eukaryotic cell" includes cells from protists (including nematodes), yeast, animals, algae, diatom, fungi, and plants.

Eukaryotic plant cells are exemplified by protocorm-like body cells, callus cells, leaf cells, stem cells, etc.).

F. Transgenic Plants

The invention further provides transgenic plants comprising the invention's DX5, DX8, DX11, and DX15 promoter sequences, portions and homologs thereof.

Plants that may be useful in the invention's methods include, without limitation, any plant that is capable of being transformed by a nucleic acid sequence using any method and that contains developing xylem cells. Thus, in one embodiment, the plant is a woody plant.

"Woody plant" refers to an angiosperm plant and/or gymnosperm plant that comprises xylem, and that forms a tree or shrub, whose stem lives for one or more years and increases in diameter each year by the addition of woody tissue. Woody plants are exemplified by, but not limited to, poplar, *eucalyptus* and pine species, including *Populus deltoids, Populus fremontii, Populus nigra, Populus tremula, Populus adenopoda, Populus alba, Populus davidiana, Populus grandidentata, Populus sieboldii, Populus tremuloides, Populus angustifolia, Populus balsamifera, Populus cathayana, Populus koreana, Populus laurifolia, Populus maximowiczii, Populus simonii, Populus szechuanica, Populus trichocarpa, Populus tristis, Populus ussuriensis, Populus yunnanensis, Populus heterophylla, Populus lasiocarpa, Populus wilsonii, Populus euphratica, Populus ilicifolia, Populus guzmanantlensis, and Populus mexicana*. Also included are *Eucalyptus grandis* and its hybrids, and *Pinus taeda*. Also included are *Pinus banksiana, Pinus brutia, Pinus caribaea, Pinus clasusa, Pinus contorta, Pinus coulteri, Pinus echinata, Pinus eldarica, Pinus ellioti, Pinus jeffreyi, Pinus lambertiana, Pinus massoniana, Pinus monticola, Pinus nigra, Pinus palustrus, pinus pinaster, Pinus ponderosa, Pinus radiata, Pinus resinosa, Pinus rigida, Pinus serotina, Pinus strobus, Pinus sylvestris, Pinus taeda, Pinus virginiana, Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata, Eucalyptus alba, Eucalyptus bancroftii, Eucalyptus botryoides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-angelica, Eucalyptus obliqua, Eucalyptus occidentalis Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo*, and *Eucalyptus youmanni*.

Wood and wood pulp obtained from plants produced using the invention's compositions and methods also are included in the invention.

In a particular embodiment, the woody plant is exemplified by angiosperm plant and gymnosperm plant.

"Angiosperm plant" refers to a vascular plant that produce seeds enclosed in an ovary.

Angiosperms are seed plants that produce flowers that bear fruit. Angiosperms are divided into dicotyledonous and monocotyledonous plants.

"Dicotyledonous plant" and "dicot plant" refer to an angiosperm plant having embryos with two seed halves or cotyledons, branching leaf veins, and flower parts in multiples of four or five. Examples of dicots include but are not limited to, *Eucalyptus, Populus, Liquidamber, Acacia*, teak, mahogany, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, and cactus.

"Monocotyledonous plant" and "monocot plant" refer to an angiosperm plant having embryos with one cotyledon or seed leaf, parallel leaf veins, and flower parts in multiples of three. Examples of monocots include, but are not limited to turfgrass, maize, rice, oat, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra* commutata (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysia japonica* (zoysiagrass), and *Dichondra micrantha*.

"Gymnosperm plant" refers to a vascular plant that bears seed without ovaries. Examples of gymnosperms include Gnetophyta, Ginkgophyta, and Cycadophyta as exemplified by conifers, cycads, ginkgos, ephedras, pine, spruce, larch, etc.

Thus in a preferred embodiment, the angiosperm plant is a dicotyledenous angiosperm plant.

Plant cells that may be manipulated using the invention's compositions and methods include cells from a totipotent body, an embryo, protoplast, callus, protocorm-like body, etc.

Transformation of a plant cell with the invention's nucleotide sequences and/or vectors may be accomplished by a variety of means known in the art including particle mediated gene transfer (see, e.g., U.S. Pat. No. 5,584,807), infection with an *Agrobacterium* strain containing the foreign DNA for random integration (U.S. Pat. No. 4,940,838) or targeted integration (U.S. Pat. No. 5,501,967) of the foreign DNA into the plant cell genome, electroinjection (Nan et al. (1995) In "Biotechnology in Agriculture and Forestry," Ed. Y. P. S. Bajaj, Springer-Verlag Berlin Heidelberg, Vol 34:145-155, Griesbach (1992) HortScience 27:620), fusion with liposomes, lysosomes, cells, minicells or other fusible lipid-surfaced bodies (Fraley et al. (1982) Proc. Natl. Acad. Sci. USA 79:1859-1863, polyethylene glycol (Krens et al. (1982) nature 296:72-74), chemicals that increase free DNA uptake, transformation using virus, and the like.

G. Regeneration of Transgenic Plants

Transformed cells may be used to regenerate plant tissue and/or a whole plant. The term "regeneration" as used herein, means growing a plant tissue and/or whole plant from a plant cell, a group of plant cells, a plant part or a plant piece (e.g., from a protoplast, callus, protocorm-like body, or tissue part). Methods for regenerating plant tissue and/or a whole plant from a totipotent body, an embryo, protoplast, callus, protocorm-like body, etc. are known in the art.

For example, plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots. Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos geminate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

EXPERIMENTAL

The following examples serve to illustrate certain embodiments and aspects of the present invention and are not to be construed as limiting the scope thereof.

Example 1

Generation of Tissue Type-Specific Transcriptomes from Poplar Stem

As a first step to gain a whole picture of the regulation of wood development, the inventors used Poplar Genome Arrays (Affymetrix, Santa Clara, Calif., USA) to generate a whole-genome transcriptional map of the wood formation with tissue type-specific manner. Poplar Genome Array has a total of 61,251 probe sets, representing 57,423 poplar gene models, and allows us to interrogate a total of 41,558 unique gene models because of the probe set redundancy. Slight redundancy of the probe sets within a single chip gave us a unique opportunity to have internal comparison of the particular genes. Actively growing young poplar stems (one-year-old) were used to collect each tissue type, such as BP (bark and mature phloem), DP (developing phloem), Ca (cambium), DX (developing xylem) and MX (mature xylem) (FIG. 1). Whole stem (WS) was used as a positive as well as an internal control. In addition, SL (SAM and leaf primordia) and ML (mature leaf without major veins) were included as negative controls for wood formation. To obtain genuine biological replications, samples were collected at two time points as a $1^{st}$ sample and a $2^{nd}$ sample during the actively growing season. The correlation coefficient values ($R^2$) of each replicated experiments were at least 0.911, indicating high reproducibility.

Example 2

Validation of Tissue Type-Specific Transcriptome

The quality of the inventors' tissue type-specific transcriptome data were analyzed first by using GeneSpring GX9 software (Agilent Technologies). Very similar distributions of the normalized intensity values for each samples and hybridization control plot gives a good estimation of the inventors' data quality and reproducibility of replicated samples. The inventors used principal component analysis (PCA) as an unbiased method of comparing the results of each tissue type-specific data set since PCA plot cluster samples with similar expression patterns for all the genes closely together. The result of PCA shows that the individual replicates clustered together and were clearly separated from those of the next tissue types, demonstrating that the data were reproducible and the resolution was sufficient to distinguish each tissue types (FIG. 2).

Contaminations among the DP, Ca and DX types were the major concerns in the inventors' sampling because these cell types are flanking each other. To clarify this possibility, the inventors checked the expressions of genes known as phloem or xylem markers in *Arabidopsis*, such as KANADI, APL (Altered Phloem Development), MAP (Microtubule-Associated Protein), and XCP2 (Xylem Cystein Peptidase 2) in the transcriptome data (FIG. 3) (Zhao et al., 2000; Kerstetter et al., 2001; Bonke et al., 2003; Rajangam et al., 2008). Results clearly show their differential expressions across the cell types. For example, poplar plant genes to orthologous KAN1 and APL have a basal level of expression in developing xylem (DX) and mature xylem (MX), while higher level of expression in DP and BP. In contrast, MAP and XCP2 orthologous genes in poplar plants are secondary xylem-specific (FIG. 3A). In addition, the gene expressions of the cellulose synthase genes were also plotted (FIG. 3B). The gene expressions of secondary wall forming cellulose synthases (PtCesA4, PtCesA7 and PtCesA4) were highly up-regulated in the wood forming cells (DX and MX), while house-keeping cellulose synthase (PtCesA2) were expressed in all the cell types. Further confirmation was performed by using a semi-quantitative RT-PCR analysis. Several genes were selected and tested their expression levels on each cell types. The expression patterns of tested genes were highly correlated with GeneChip data. These data strongly indicate that the tissue type-specific transcriptome obtained by the inventors is sufficiently reliable to move forward to further analysis.

Example 3

Identification of Developing Xylem-Specific Transcripts

To isolate developing xylem-specific probe sets, the inventors developed very stringent filters by using Excel software (Microsoft). By applying filters selecting transcripts having more than 10 fold up-regulation in DX against SL, ML, BP, DP and Ca, respectively, the inventors narrowed down to only 81 probe sets, which are very specific to DX. Following additional filter selecting probe sets having at least 2,000 of signal intensity in DX, which is more than three-fold of average signal intensity of whole transcriptome data, the inventors finally obtained a total of 47 probe sets. The resulting probe sets are not only highly specific to DX but also produced high level expression in DX (FIG. 4). Several genes previously known as xylem-specific expression, such as fasciclin-like arabinogalactan proteins, XCP1 (Xylem Cysteine Peptidase 1), XCP2, ACC oxidase and laccases, were included in this list.

Among these, the inventors further selected five transcripts and confirmed their developing xylem cell-specific and/or developing xylem tissue-specific expression by using semi-quantitative RT-PCR (FIG. 5). Based on this result, the inventors chose DX5 as the inventors' first target for further study. DX5 (i.e., PtrNAC073) is orthologous to ANAC073, a NAC family transcription factor of *Arabidopsis*, based on the sequence homology and expression pattern.

Example 4

Promoter Activity in the Transgenic Plants

To check the promoter activity in planta, promoter regions of PtrNAC073 and ANAC073 genes were transcriptionally fused with the GUS gene and introduced into poplar plants. For GUS assay, the inventors examined all parts of transgenic poplar plants, including young and old leaves, petiole, shoot apical meristem and stem, after transferring to soil and grow for 6 weeks. GUS activity driven by PtrNAC073 promoter specifically observed in the developing xylem cells of stem cross-section (FIG. 6A), with no expression in leaf tissue. Like as PtrNAC073, promoter activity of ANAC073 was found in the developing xylem cells (FIG. 6B).

The GUS activity directed by PtrNAC073 promoter in planta was consistent with the expression pattern of PtrNAC073 gene, which is developing xylem-specific. Promoter of ANAC073 gene also showed similar GUS activity. These results suggest that the promoter of PtrNAC073 is useful for xylem-specific expression.

Xylem-specific expression, and in particular, developing xylem-specific expression is by each of DX5 promoter sequence listed as SEQ ID NO:02, DX8 promoter sequence listed as SEQ ID NO:04, DX11 promoter sequence listed as SEQ ID NO:06, and DX15 promoter sequence listed as SEQ ID NO:08, is shown in FIG. 10.

SOME REFERENCES

Bonke et al. (2003) Nature, 426, 181-186.
Curtis et al. (2003) Plant Physiol, 133, 462-469.
Han et al. (2000) Plant Cell Reports 19, 315-320.
Hu et al. (1999) Nat Biotechnol, 17, 808-812.
Jones et al. (2001) Plant J, 26, 205-216.
Kerstetter et al. (2001) Nature, 411, 706-709.
Leple et al. (1992) Plant Cell Reports 11, 137-141.
Li et al. (2003) Proc Natl Acad Sci USA, 100, 4939-4944.
Murashige et al. (1962) Physiol. Plant. 15, 473-479
Rajangam et al. (2008) Plant Physiol, 148, 1283-1294.
Song et al. (2006) Plant Cell Physiol, 47, 1582-1589.
Teymouri et al. (2005) Bioresour Technol, 96, 2014-2018.
Turner et al. (1997) Plant Cell, 9, 689-701.
Xiang et al. (1999) Plant Mol Biol, 40, 711-717.
Zhao et al. (2000) Plant Physiol, 123, 1185-1196.

Each and every publication and patent mentioned in the above specification is herein incorporated by reference. Various modifications and variations of the described compositions and methods of the invention will be apparent to those skilled in the art without departing from the scope and spirit of the invention. Although the invention has been described in connection with specific preferred embodiment, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A recombinant nucleic acid comprising a first nucleic acid segment with at least 98% sequence identity to SEQ ID NO: 08 that is operably-linked to a heterologous second nucleic acid.

2. The nucleic acid of claim 1, wherein said first nucleic acid segment drives developing xylem expression of the operably-linked second nucleic acid in a plant cell.

3. The nucleic acid of claim 2, wherein said second nucleic acid encodes
   (a) a polypeptide involved in biosynthesis of a polysaccharide selected from cellulose and lignin,
   (b) an antisense RNA of a sequence involved in biosynthesis of a polysaccharide selected from cellulose and lignin, or
   (c) an interference RNA (iRNA) of a sequence involved in biosynthesis of a polysaccharide selected from cellulose and lignin.

4. An expression vector comprising the recombinant nucleic acid of claim 1.

5. A cell comprising the recombinant nucleic acid of claim 1.

6. The cell of claim 5, wherein said cell is selected from a bacterial cell, a mammalian cell, an insect cell, a plant cell, and a fungal cell.

7. The cell of claim 6, wherein said plant cell is selected from a developing xylem cell and a seed cell.

8. A transgenic plant comprising the recombinant nucleic acid of claim 1.

9. The transgenic plant of claim 8, wherein said heterologous second nucleic acid encodes a sequence selected from the group of (a) a polypeptide involved in biosynthesis of a polysaccharide selected from cellulose and lignin,
(b) an antisense RNA of a sequence involved in biosynthesis of a polysaccharide selected from cellulose and lignin, and
(c) an interference RNA (iRNA) of a sequence involved in biosynthesis of a polysaccharide selected from cellulose and lignin.

10. A seed comprising the recombinant nucleic acid of claim 1.

11. A composition comprising xylem, wherein said xylem comprises the recombinant nucleic acid of claim 1.

12. A method for expressing a polypeptide or RNA from a nucleic acid in a plant cell comprising
a) providing
i) an expression vector comprising the recombinant nucleic acid of claim 1, wherein the second nucleic acid encodes a polypeptide or an RNA, and
ii) a plant cell,
b) introducing the expression vector into said plant cell to produce a transgenic plant cell, and culturing the transgenic plant cell under conditions for expression of said polypeptide or RNA from said second nucleic acid in said transgenic plant cell.

13. The method of claim 12, further comprising c) detecting expression of said polypeptide or RNA from said second nucleic acid in said transgenic cell.

14. The method of claim 12, wherein said second nucleic acid encodes
(a) a polypeptide involved in biosynthesis of a polysaccharide selected from cellulose and lignin,
(b) an antisense RNA of a sequence involved in biosynthesis of a polysaccharide selected froth cellulose and lignin, or
(c) an interference RNA (iRNA) of a sequence involved in biosynthesis of a polysaccharide selected from cellulose and lignin.

15. The method of claim 12, further comprising c) regenerating a transgenic plant from said transgenic plant cell.

16. The method of claim 15, further comprising d) detecting expression of said polypeptide or RNA from said second nucleic acid in a developing xylem cell of said transgenic plant.

17. The method of claim 12, wherein the heterologous second nucleic acid encodes an enzyme.

* * * * *

UNITED STATES PATENT AND TRADEMARK OFFICE
CERTIFICATE OF CORRECTION

| | | |
|---|---|---|
| PATENT NO. | : 9,845,478 B2 | Page 1 of 1 |
| APPLICATION NO. | : 13/821095 | |
| DATED | : December 19, 2017 | |
| INVENTOR(S) | : Han et al. | |

It is certified that error appears in the above-identified patent and that said Letters Patent is hereby corrected as shown below:

On the Title Page

On page 2, in Column 1, item (56), under "Other Publications", Line 8, delete "xylem-specifci" and insert --xylem-specific-- therefor On page 2, in Column 2, item (56), under "Other Publications", Line 4, delete "Planta"," and insert --Plants",-- therefor On page 2, in Column 2, item (56), under "Other Publications", Line 58, delete "Consruction" and insert --Construction-- therefor In the Claims In Column 37, Line 61, in Claim 3, after "encodes", insert --:--

In Column 38, Line 67, in Claim 9, after "of", insert --:--

In Column 39, Line 13, in Claim 12, after "comprising", insert --:--

In Column 39, Line 14, in Claim 12, after "providing", insert --:--

In Column 40, Line 5, in Claim 14, after "encodes", insert --:--

In Column 40, Line 9, in Claim 14, delete "froth" and insert --from-- therefor

Signed and Sealed this
Sixteenth Day of July, 2019

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 1941
<212> TYPE: DNA
<213> ORGANISM: Populus trichocarpa

<400> SEQUENCE: 1
ggggcagatg ataccttgat acttggacta ggaatattca aaggagaaaa tattgatgtg      60
tatatttgta cttaattatg cacatctctt tcactttgtt gtaagctggc aatatacaac     120
acaagaatgg tctttatgct ttgattttct tttctcacaa gaaggtagat attggctttt     180
taccgaaatg aatattgctt gagctagaga atacatcaag tatcgtaaag ggcacccccaa    240 attcttacag cctcgtgatg cacgttttgt tcttcaaaat ctaggggaaa ttcattaatt     300
gaaggtcgga tctgtaggta gaatttccct tttctttta atggaatttg atgaaagaca     360
ctgtagcaat aatttaaaag gaaattaagt aagttcacgg ttttttgatgg tttttcccga    420
```

```
gttgattgga tcgcagatta acctgagttt ttaaacggat tacatcaatt aaattttttgt   480 ttattttttat tgaaatttag tctaatctaa atcccgggtt attcaatccg tcgaataatc   540
aagtaagttt ataaaaaaaa tataataaaa gacaataaag gctaactatt tgtgtgggaa   600
gcagacaatt ccgatggtgt aagaaatttg tgttgtcatt ttttatttat taaattgctc   660 tccttttta caggaatgtt ataaatacaa ggacatataa ttcagctcaa taaatctttt   720
ggctttaatt tattttcctt ggaacaaggg gctgttacca aatatggagc actgtgcttg   780
tgtcatgcat gtaggtaagg ggggaaaaaa ctaaggaatt tagctgagaa agaggttgtc   840
aatttactgt gatagatagg ttccttgctt tacatgagaa gtctacgtga agaaatggaa   900
ttatatattt ggttggacat tggctctctt aatatttatt aattattatt ccattttatc   960
ctgtgatatt aaacctaact cctcttgaat aatcgggttg aattgatatt taattaactt  1020
gatatatcaa gtatcaaaac ttaatttgat attttttaaaa ataatattgt tttgattttt  1080
tttaaatatt gatttagatt attttttata atttgaatca tagttagata aattttgagt  1140
taggttttat aattattatt ttattagttt ctttcttatt tatgtttttc aatattaagg  1200
agtttataca ttagctttgt tcacactcta ggttgacatt ggagctgaaa tatctctctc  1260
tatgaggtgg tgaaatagct ctcacgcatc agattgcccc atctccactc aaccctaact  1320
agccatgatt aatattttat ttctttttttt tttaattttt ttaatctttta aaacttattt  1380 caagcagaaa acatgccctt tagacggagt aaaaaggacc ctaaaactac atttattgtc  1440
ctacaagttt tcataagcat cccatttaca taagcacacc accaaactta agatccaagc  1500
aaccctaaaa ttttccttttc tttgcaacat actactacta ctgcattttt ggaaattaca  1560
ccatattttg attttttagg tatacctttc tctctctctc tctctctctc ccactctctc  1620
gagaaaggac aaagaggtgg tagggggggag gggagaggag aggagaggag agtgtgcatg  1680
ttgtctcatg caaagtggga ggagaattta attccttccc tacccctaaag atcaagagct  1740 atctatgtct tgaagaaaga caatacatgc tttagaagga gacaaattgc ttttccttct  1800
tttcttttaa gcccttcgtg tctctctcttc acacacacac acgcatcata catagtctttt  1860 gtctattttg gagtagcagt tgtcgaggga gagagcaaga aagaaaggtg tgcaatatat  1920
gggcataaga ggaaaccaaa g                                            1941

<210> SEQ ID NO 2
<211> LENGTH: 1918
<212> TYPE: DNA
<213> ORGANISM: Populus trichocarpa

<400> SEQUENCE: 2
ggggcagatg atacccttgat acttggacta ggaatattca aaggagaaaa tattgatgtg    60
tatatttgta cttaattatg cacatctctt tcactttgtt gtaagctggc aatatacaac   120
acaagaatgg tctttatgct ttgatttttct tttctcacaa gaaggtagat attggctttt   180
taccgaaatg aatattgctt gagctagaga atacatcaag tatcgtaaag gcaccccaa    240 attcttacag cctcgtgatg cacgttttgt tcttcaaaat ctaggggaaa ttcattaatt   300
gaaggtcgga tctgtaggta gaatttccct ttttctttta atggaatttg atgaaagaca   360
ctgtagcaat aatttaaaag gaaattaagt aagttcacgg ttttttgatgg tttttcccga   420 gttgattgga tcgcagatta acctgagttt ttaaacggat tacatcaatt aaattttttgt   480 ttattttttat tgaaatttag tctaatctaa atcccgggtt attcaatccg tcgaataatc   540
```

```
aagtaagttt ataaaaaaaa tataataaaa gacaataaag gctaactatt tgtgtgggaa      600
gcagacaatt ccgatggtgt aagaaatttg tgttgtcatt ttttatttat taaattgctc      660
tcctttttta caggaatgtt ataaatacaa ggacatataa ttcagctcaa taaatctttt      720
ggctttaatt tattttcctt ggaacaaggg gctgttacca aatatggagc actgtgcttg      780
tgtcatgcat gtaggtaagg ggggaaaaaa ctaaggaatt tagctgagaa agaggttgtc      840
aatttactgt gatagatagg ttccttgctt tacatgagaa gtctacgtga agaaatggaa      900
ttatatattt ggttggacat tggctctctt aatatttatt aattattatt ccattttatc      960
ctgtgatatt aaacctaact cctcttgaat aatcgggttg aattgatatt taattaactt     1020
gatatatcaa gtatcaaaac ttaatttgat atttttaaaa ataatattgt tttgattttt     1080
tttaaatatt gatttagatt atttttata atttgaatca tagttagata aattttgagt     1140
taggttttat aattattatt ttattagttt ctttcttatt tatgttttc aatattaagg     1200 agtttataca ttagctttgt tcacactcta ggttgacatt ggagctgaaa tatctctctc     1260
tatgaggtgg tgaaatagct ctcacgcatc agattgcccc atctccactc aaccctaact     1320
agccatgatt aatattttat ttcttttttt tttaattttt ttaatcttta aaacttattt     1380
caagcagaaa aacatgcctt tagacggagt aaaaaggacc ctaaaactac atttattgtc     1440
ctacaagttt tcataagcat cccatttaca taagcacacc accaaactta agatccaagc     1500
aaccctaaaa ttttcctttc tttgcaacat actactacta ctgcatttt ggaaattaca     1560 ccatattttg attttttagg tatacctttc tctctctctc tctctctctc ccactctctc     1620
gagaaaggac aaagaggtgg tagggggggag gggagaggag aggagaggag agtgtgcatg     1680
ttgtctcatg caaaagtgga ggagaattta attccttccc tacctaaag atcaagagct     1740 atctatgtct tgaagaaaga caatacatgc tttagaagga gacaaattgc ttttccttct     1800
tttcttttaa gcccttcgtg tctctcttcc acacacacac acgcatcata catagtcttt     1860
gtctattttg gagtagcagt tgtcgaggga gagagcaaga aagaaaggtg tgcaatat        1918

<210> SEQ ID NO 3
<211> LENGTH: 1517
<212> TYPE: DNA
<213> ORGANISM: Populus trichocarpa

<400> SEQUENCE: 3
tccattctac tggacttccc acctcaccca actccgaaag agtcctctca actagaaagg       60
aaaaaaaaaa gaaagaggta aattaaaaaa aatcacaaca acgtaaacag actttcattt      120
ttgtacctga agagtttgag ggaggaactt ggttccaaca ttgaggaaca acatggctaa      180
gagatcagat tttgcacaga agctgttgga agatctccgg tcgaggaagg aacgaatggc      240
tgtatctcat agctcagaag gttcaaaatc agctgctcca ggttagtatt ctattatatt      300
tcacaattta ttttcttcag ctccaaaaca aaattgaaaa tttagaaggc ttaaagcaag      360
taaaagctat ggtttaagac tatcacgcaa cttgaaaagc tatcatgcct ctaaacatga      420
agaatcgcaa gtttttatca tcagttcagt tctcatcaga agtgtaaaat taatagctag      480
gtctctaaac taaattaatg attattctta ctcaatgacc ttacctgctc ttttaagtaa      540
agtataagaa gattatttgg atggccgatt tggaatacaa aagagcaggg attaatagaa      600
agtatgaaat ggctaagtta agaaaataaa aataaattca gacacctcgc tgatgacaga      660
agcagggcct gccttccacc ttcattcaaa acgatagaa caaggagcaa gtaacctagt      720
ctcgtagtag tataataatg ctacttgtga tgcagtttcc caaccaaaaa ctcttgtgat      780
```

```
atgctaataa tgctctgttc cagaaaaatc taaaaatgaa cagaaacttg atgaaaacag      840
tggcgaaggg taagatgaaa gaaaaccaaa tattaaagct ttacaccctc tcatatgtaa      900
agagcacaaa atgaaaagga aaagaaaatc aattcatcca ttgcaaaata tttatatgag      960
aattccaatt ttccagtatt ttctattttc aaaagaata aataggaaaa gaaaaaaaag     1020
acattttcta tagtgtgaac tgtgtgagaa gaagcaatat tagcgcttta ttttcaatac     1080
taagagaaat aaaatgtcag gaaatgatct aaaactagat agtgacatct agtcttctag     1140
catacaaaaa ttcctgcatt tccattactt agtacgaagt atcatcattg ttttctctgc     1200
atcgtgtgct tgtgcagatg tacatgctta ttccaagcaa atacacagag gatccagaga     1260
tatgaagacc catagaagtg taagtatcat ggctcaagct tatcacagtt ttaggtatta     1320
taaattccca atttactcga actgttccat gaccacagaa tggcattaga agtggaagtg     1380
tgcacagtag aactagtgga agtaatatag cactctccat tgaagaagtt tcaacagaga     1440
ttgttccatt tggggaggt cgaaactccg aacaaatagg agatctgtcc atggcactgg     1500
cttttgccct tgagaat                                                     1517

<210> SEQ ID NO 4
<211> LENGTH: 1490
<212> TYPE: DNA
<213> ORGANISM: Populus trichocarpa

<400> SEQUENCE: 4
tccattctac tggacttccc acctcaccca actccgaaag agtcctctca actagaaagg       60 aaaaaaaaa gaaagaggta aattaaaaaa aatcacaaca acgtaaacag actttcattt      120
ttgtacctga agagtttgag ggaggaactt ggttccaaca ttgaggaaca acatggctaa      180
gagatcagat tttgcacaga agctgttgga agatctccgg tcgaggaagg aacgaatggc      240
tgtatctcat agctcagaag gttcaaaatc agctgctcca ggttagtatt ctattatatt      300
tcacaattta ttttcttcag ctccaaaaca aaattgaaaa tttagaaggc ttaaagcaag      360
taaaagctat ggtttaagac tatcacgcaa cttgaaaagc tatcatgcct ctaaacatga      420
agaatcgcaa gttttatca tcagttcagt tctcatcaga agtgtaaaat taatagctag      480
gtctctaaac taaattaatg attattctta ctcaatgacc ttacctgctc ttttaagtaa      540
agtataagaa gattatttgg atggccgatt tggaatacaa aagagcaggg attaatagaa      600
agtatgaaat ggctaagtta agaaaataaa aataaattca gacacctcgc tgatgacaga      660
agcagggcct gccttccacc ttcattcaaa acgatagaa caaggagcaa gtaacctagt      720
ctcgtagtag tataataatg ctacttgtga tgcagtttcc caaccaaaaa ctcttgtgat      780
atgctaataa tgctctgttc cagaaaaatc taaaaatgaa cagaaacttg atgaaaacag      840
tggcgaaggg taagatgaaa gaaaaccaaa tattaaagct ttacaccctc tcatatgtaa      900
agagcacaaa atgaaaagga aaagaaaatc aattcatcca ttgcaaaata tttatatgag      960
aattccaatt ttccagtatt ttctattttc aaaagaata aataggaaaa gaaaaaaaag     1020
acattttcta tagtgtgaac tgtgtgagaa gaagcaatat tagcgcttta ttttcaatac     1080
taagagaaat aaaatgtcag gaaatgatct aaaactagat agtgacatct agtcttctag     1140
catacaaaaa ttcctgcatt tccattactt agtacgaagt atcatcattg ttttctctgc     1200
atcgtgtgct tgtgcagatg tacatgctta ttccaagcaa atacacagag gatccagaga     1260
tatgaagacc catagaagtg taagtatcat ggctcaagct tatcacagtt ttaggtatta     1320
```

| taaattccca atttactcga actgttccat gaccacagaa tggcattaga agtggaagtg | 1380 |
| tgcacagtag aactagtgga agtaatatag cactctccat tgaagaagtt tcaacagaga | 1440 |
| ttgttccatt tggggaggt cgaaactccg aacaaatagg agatctgtcc | 1490 |

<210> SEQ ID NO 5
<211> LENGTH: 1315
<212> TYPE: DNA
<213> ORGANISM: Populus trichocarpa

<400> SEQUENCE: 5

| agtcggtatt tcagtacttg gggccatgaa gtcagtagtg aagtctaata aatattctta | 60 |
| agttgcaagt ctctcttctg tcgcccacgt tctcttcttt gccctttctt tttctttcac | 120 |
| atccacagcc tctttgaaac tatactgtaa tgaataataa tcaaaaccaa gttcctgttc | 180 |
| cttgtttgtg gttttttctc tccaaatttt gttatcttat ctttctatga tccctctctt | 240 |
| ctctcactcc cacctcacaa gttttttaaa aaaacaaatt gttcatcggg cttgtgacta | 300 |
| gaagaagact gcttaccatg ttttctttt tcgaatacaa cttcaaaaga aaaaaaaatg | 360 |
| tgtcaaaaaa ggtgaactag gtggagtgtt gtgttgacaa tgattcagta cccgtcatgg | 420 |
| acgggatgat taagatgtca agtgctatta caactcaaaa gcattattgc atcatctgta | 480 |
| ccgtaatgaa attcaatgat aatccattag cacccagagc cgtcgagaaa ggaaatgttt | 540 |
| agaagtacaa tagtgagtaa ttttcaatca aaattataaa tatattaaaa tattatttt | 600 |
| tttatttttt aaaaattaat tttaatatca taatctgatc atactaaaaa aatatttta | 660 |
| aaacataaaa agcgaaaaaa atatcaacaa cgaattgtaa atggccacct aatcataata | 720 |
| tgcgggaatt aaattctgtg tggccaaatt taccagaaga tagaagctga aaatgagctg | 780 |
| acaggttagc agatgatctt gatcgtggtt ttctctggaa gacttgcttg ttcgagaact | 840 |
| taacaaagga cacaagctgt tgttgttttc atttggcaca ggttgcttat gaatcaagtt | 900 |
| caccaacaaa acaaaaacag agagataaaa gggaaaggtt cggttaactg ctgctaaata | 960 |
| gaagtcatgt gtgtccctga caagaaact ccaactttat gtcttaatta tgagaaattt | 1020 |
| ttaccacctt aaatttaaat aagagtgcag gagagatata acccaaagct tcagcgtcac | 1080 |
| ctacttctgc agtcttacct tttaagcaaa tacacgcacc aaagttccca gccatcattc | 1140 |
| tctatctttt ccattccctc tcaatacttg gttgattttc aagcaactca aaacagaatg | 1200 |
| ctaccagagt ttagcagtcc aggaacctct cacagcactt ccacgtttta gcaatccaaa | 1260 |
| tattcctgag ttgcggcaag gcaatatctt agaggccgtc agatgggttc gttcc | 1315 |

<210> SEQ ID NO 6
<211> LENGTH: 1302
<212> TYPE: DNA
<213> ORGANISM: Populus trichocarpa

<400> SEQUENCE: 6

| agtcggtatt tcagtacttg gggccatgaa gtcagtagtg aagtctaata aatattctta | 60 |
| agttgcaagt ctctcttctg tcgcccacgt tctcttcttt gccctttctt tttctttcac | 120 |
| atccacagcc tctttgaaac tatactgtaa tgaataataa tcaaaaccaa gttcctgttc | 180 |
| cttgtttgtg gttttttctc tccaaatttt gttatcttat ctttctatga tccctctctt | 240 |
| ctctcactcc cacctcacaa gttttttaaa aaaacaaatt gttcatcggg cttgtgacta | 300 |
| gaagaagact gcttaccatg ttttctttt tcgaatacaa cttcaaaaga aaaaaaaatg | 360 |
| tgtcaaaaaa ggtgaactag gtggagtgtt gtgttgacaa tgattcagta cccgtcatgg | 420 |

```
acgggatgat taagatgtca agtgctatta caactcaaaa gcattattgc atcatctgta      480
ccgtaatgaa attcaatgat aatccattag cacccagagc cgtcgagaaa ggaaatgttt      540
agaagtacaa tagtgagtaa ttttcaatca aattataaaa tatattaaaa tattatttttt     600 tttattttttt aaaaattaat tttaatatca taatctgatc atactaaaaa aatattttta    660
aaacataaaa agcgaaaaaa atatcaacaa cgaattgtaa atggccacct aatcataata      720
tgcgggaatt aaattctgtg tggccaaatt taccagaaga tagaagctga aaatgagctg      780
acaggttagc agatgatctt gatcgtggtt ttctctggaa gacttgcttg ttcgagaact      840
taacaaagga cacaagctgt tgttgttttc atttggcaca ggttgcttat gaatcaagtt      900
caccaacaaa acaaaaacag agagataaaa gggaaaggtt cggttaactg ctgctaaata      960
gaagtcatgt gtgtccctga acaagaaact ccaactttat gtcttaatta tgagaaattt     1020
ttaccacctt aaatttaaat aagagtgcag gagagatata acccaaagct tcagcgtcac     1080
ctacttctgc agtcttacct tttaagcaaa tacacgcacc aaagttccca gccatcattc     1140
tctatctttt ccattccctc tcaatacttg gttgattttc aagcaactca aaacagaatg     1200
ctaccagagt ttagcagtcc aggaacctct cacagcactt ccacgtttta gcaatccaaa     1260
tattcctgag ttgcggcaag gcaatatctt agaggccgtc ag                        1302

<210> SEQ ID NO 7
<211> LENGTH: 1025
<212> TYPE: DNA
<213> ORGANISM: Populus trichocarpa

<400> SEQUENCE: 7 ttccccctttt tggttcaatg ccttttattc ttccaaaatt atttcatatt ttgtatccgg      60
aggacatatt tgtttcaaaa ggtgtcagaa aatcaaagcc cattgaaaat atataaacat     120
atatagagat aaaaactcaa gggttcattc caaaatataa gaacaaactg attgaattaa     180
tttgttattt taagaacact gtctatatgt ttatatagtg ggaggtagtg ttttttaaat     240
catatactaa cttattataa aaataaatca taaaaaagga acctcaagca tcccctggta     300
agctcgtatg taggaatact cggagatcaa atgtccgaat gtcaaatgtt aaggcaagtg     360
aaatatccct gacttttag caagcaaatt gttgagtagc taaaatgaat tattttaata     420 ttttaaatc attttaatat attaatatta aaaaaaatta aatattttttt ttaatacatt     480 ttcaataaca aacactttaa aatataatct ttgtcacact cttaaacagt aacagcagaa     540
agcatatgtg agtgatatag ctatagttgc tgtttgacac ggacaatctc catctaaatt     600
catgaataat aaagttttgc ctacacaccc acttgaaatc tcctcctagt ttcctgatt      660 tgccatgcta actacaagaa caagatgcta gctagtatct tgttctgtct ctcgctctct     720
ctctatctct ccagttgata gttgatagtt gatagttgat agctgatacc ctcccacctt     780
tcccagaaag atgattgagg aactagtcac tgtgttcgtg taactaatac tgttcatggc     840
acctaacttg atcctctctt caccagacca ctataaaaac cctatctgtc ctcctcataa     900
tcatatcact acacccaaca cttctgcaag cacaactcca ttcaagaaca tcaagagtat     960
aggccgccgc tgcaacaaaa cagcactcct agctacttca agatgaggcc acaatctttc    1020
atctt                                                                1025

<210> SEQ ID NO 8
<211> LENGTH: 1002
<212> TYPE: DNA
```

<213> ORGANISM: Populus trichocarpa

<400> SEQUENCE: 8

| | | | | | | |
|---|---|---|---|---|---|---|
| ttcccccttt | tggttcaatg | ccttttattc | ttccaaaatt | atttcatatt | ttgtatccgg | 60 |
| aggacatatt | tgtttcaaaa | ggtgtcagaa | aatcaaagcc | cattgaaaat | atataaacat | 120 |
| atatagatat | aaaaactcaa | gggttcattc | caaaatataa | gaacaaactg | attgaattaa | 180 |
| tttgttattt | taagaacact | gtctatatgt | ttatatagtg | ggaggtagtg | ttttttaaat | 240 |
| catatactaa | cttattataa | aaataaatca | taaaaaagga | acctcaagca | tcccctggta | 300 |
| agctcgtatg | taggaatact | cggagatcaa | atgtccgaat | gtcaaatgtt | aaggcaagtg | 360 |
| aaatatccct | gacttttag | caagcaaatt | gttgagtagc | taaaatgaat | tattttaata | 420 |
| ttttaaatc | attttaatat | attaatatta | aaaaaaatta | aatattttt | ttaatacatt | 480 |
| ttcaataaca | aacactttaa | aatataatct | ttgtcacact | cttaaacagt | aacagcagaa | 540 |
| agcatatgtg | agtgatatag | ctatagttgc | tgtttgacac | ggacaatctc | catctaaatt | 600 |
| catgaataat | aaagttttgc | ctacacaccc | acttgaaatc | tcctcctagt | tttcctgatt | 660 |
| tgccatgcta | actacaagaa | caagatgcta | gctagtatct | tgttctgtct | ctcgctctct | 720 |
| ctctatctct | ccagttgata | gttgatagtt | gatagttgat | agctgatacc | ctcccacctt | 780 |
| tcccagaaag | atgattgagg | aactagtcac | tgtgttcgtg | taactaatac | tgttcatggc | 840 |
| acctaacttg | atcctctctt | caccagacca | ctataaaaac | cctatctgtc | ctcctcataa | 900 |
| tcatatcact | acacccaaca | cttctgcaag | cacaactcca | ttcaagaaca | tcaagagtat | 960 |
| aggccgccgc | tgcaacaaaa | cagcactcct | agctacttca | ag | | 1002 |

<210> SEQ ID NO 9
<211> LENGTH: 1236
<212> TYPE: DNA
<213> ORGANISM: Populus trichocarpa

<400> SEQUENCE: 9

| | | | | | | |
|---|---|---|---|---|---|---|
| ttcccccttt | tggttcaatg | ccttttattc | ttccaaatta | atttcaatat | tttatatccg | 60 |
| gaggaacata | tttgtttcaa | aaggtgtcag | aaaatcaaag | cccattgaaa | atatataaac | 120 |
| atatatagat | ataaaaactc | aaggattcat | tccaaaatat | aagaacaaac | tgattgaatt | 180 |
| aatttgttat | tttaagaaca | ctgtctatat | gtttttttt | agtttaacgt | gggtgtccgg | 240 |
| gccagcttgc | gcgcacctca | actaatccca | cgggtcctga | agttaacgat | catgtaagtc | 300 |
| tccagtagcc | atcatatgag | caaccacagg | gctcgaacct | gagaccacag | aaggagcaaa | 360 |
| cctcttggtc | ccaaactctt | accattgagc | taccatctag | atggttacac | tgtctatata | 420 |
| tttatatagt | ggtaggtagt | gttttttaaa | tcatatacta | acttattata | aaaataaatc | 480 |
| ataaaaaagg | aacctcaagc | atccctttgt | aagctcgtat | gtaggaatac | tcggagatca | 540 |
| aatgtccgaa | tgtcaaatgt | taaggcaagt | gaaatatccc | tgacttttta | gcaagcaaat | 600 |
| tgttgagtag | ctaaaatgaa | ttatttaat | atttttaaat | cattttaata | tattaatatt | 660 |
| aaaaaaaatt | aaatattttt | tttaatacat | tttcaataac | aaacacttta | aaatataatc | 720 |
| tttgtcacac | tcttaaacag | taacagcaga | agcatatgt | gagtgatata | gctatagttg | 780 |
| ctgtttgaca | cggacaatct | ccatctaaat | tcatgaataa | taaagttttg | cctacacacc | 840 |
| cacttgaaat | ctcctcctag | ttttcctgat | ttgccatgct | aactacaaga | acaagatgct | 900 |
| agctagtatc | ttgttctgtc | tctcgctctc | tctctatctc | tccagttgat | agttgatagt | 960 |
| tgatagttga | tagctgatac | actcccacct | ttcccagaaa | gatgattgag | gaactagtca | 1020 |

-continued

```
ctgtgttcgt gtaactaata ctgttcatgg cacctaactt gatcctctct tcaccagacc    1080
actataaaaa ccctatctgt cctcctcata atcatctcac tacacccaac acttctgcaa    1140
gcacaactcc attcaagaac atcaagagta taggccgcca ctgcaacaaa acagcactcc    1200
tagctacttc aagatgaggc cacaatcttt catctt                              1236
```

<210> SEQ ID NO 10
<211> LENGTH: 1213
<212> TYPE: DNA
<213> ORGANISM: Populus trichocarpa

<400> SEQUENCE: 10

```
ttcccccttt tggttcaatg ccttttattc ttccaaatta atttcaatat tttatatccg      60
gaggaacata tttgtttcaa aaggtgtcag aaaatcaaag cccattgaaa atatataaac     120
atatatagat ataaaaactc aaggattcat tccaaaatat aagaacaaac tgattgaatt     180
aatttgttat tttaagaaca ctgtctatat gttttttttt agtttaacgt gggtgtccgg     240
gccagcttgc gcgcacctca actaatccca cgggtcctga agttaacgat catgtaagtc     300
tccagtagcc atcatatgag caaccacagg gctcgaacct gagaccacag aaggagcaaa     360
cctcttggtc ccaaactctt accattgagc taccatctag atggttacac tgtctatata     420
tttatatagt ggtaggtagt gtttttaaaa tcatatacta acttattata aaaataaatc     480
ataaaaaagg aacctcaagc atccctttgt aagctcgtat gtaggaatac tcggagatca     540
aatgtccgaa tgtcaaatgt taaggcaagt gaaatatccc taacttttta gcaagcaaat     600
tgttgagtag ctaaaatgaa ttattttaat attttttaaat cattttaata tattaatatt     660
aaaaaaaatt aaatattttt tttaatacat tttcaataac aaaacacttta aaatataatc     720 tttgtcacac tcttaaacag taacagcaga aagcatatgt gagtgatata gctatagttg     780
ctgtttgaca cggacaatct ccatctaaat tcatgaataa taaagttttg cctacacacc     840
cacttgaaat ctcctcctag ttttcctgat ttgccatgct aactacaaga acaagatgct     900
agctagtatc ttgttctgtc tctcgctctc tctctatctc tccagttgat agttgatagt     960
tgatagttga tagctgatac actcccacct ttcccagaaa gatgattgag gaactagtca    1020
ctgtgttcgt gtaactaata ctgttcatgg cacctaactt gatcctctct tcaccagacc    1080
actataaaaa ccctatctgt cctcctcata atcatctcac tacacccaac acttctgcaa    1140
gcacaactcc attcaagaac atcaagagta taggccgcca ctgcaacaaa acagcactcc    1200
tagctacttc aag                                                       1213
```